(12) United States Patent
Daniels et al.

(10) Patent No.: US 11,816,978 B1
(45) Date of Patent: Nov. 14, 2023

(54) SYSTEM, DEVICE, METHOD AND PROGRAM PRODUCT TO PROVIDE HEALTHCARE AT A REMOTE LOCATION

(71) Applicant: JDTC Inc., Roslyn Heights, NY (US)

(72) Inventors: Joseph Jonathan Daniels, Roslyn Heights, NY (US); Kenneth Francis Martin, Jr., Franklin Square, NY (US)

(73) Assignee: JDTC Inc., Roslyn Heights, NY (US)

( * ) Notice: Subject to any disclaimer, the term of this patent is extended or adjusted under 35 U.S.C. 154(b) by 417 days.

(21) Appl. No.: 17/214,380

(22) Filed: Mar. 26, 2021

Related U.S. Application Data

(60) Provisional application No. 63/003,567, filed on Apr. 1, 2020.

(51) Int. Cl.
| | | |
|---|---|---|
| H04B 10/11 | (2013.01) | |
| H04B 10/114 | (2013.01) | |
| G08B 7/06 | (2006.01) | |
| H04B 1/02 | (2006.01) | |
| G16H 40/67 | (2018.01) | |
| G08B 17/10 | (2006.01) | |

(52) U.S. Cl.
CPC ............. *G08B 7/06* (2013.01); *G08B 17/10* (2013.01); *G16H 40/67* (2018.01); *H04B 1/02* (2013.01); *H04B 10/11* (2013.01); *H04B 10/1149* (2013.01)

(58) Field of Classification Search
CPC ...... H04B 10/11; H04B 10/1149; H04B 1/02; G08B 7/06; G16H 40/67

USPC ............... 398/118, 127, 140, 151, 182, 202
See application file for complete search history.

(56) References Cited

U.S. PATENT DOCUMENTS

| | | | |
|---|---|---|---|
| 2006/0154642 A1* | 7/2006 | Scannell | G08B 7/066 455/404.1 |
| 2013/0301034 A1* | 11/2013 | Olds | H05B 47/11 356/218 |
| 2016/0232010 A1* | 8/2016 | Dicks | G16H 40/67 |
| 2018/0353358 A1* | 12/2018 | Lingegård | A61G 7/012 |
| 2021/0257075 A1* | 8/2021 | Edwards | A61M 5/1723 |

FOREIGN PATENT DOCUMENTS

| | | | | |
|---|---|---|---|---|
| CA | 2957199 A1 * | 6/2010 | | H05B 45/10 |
| CN | 110335449 A * | 10/2019 | | |
| EP | 3974300 A1 * | 3/2022 | | |

* cited by examiner

*Primary Examiner* — Li Liu
(74) *Attorney, Agent, or Firm* — Amster, Rothstein & Ebenstein LLP

(57) ABSTRACT

Systems and methods for a portable electronic device to provide healthcare to a subject at a remote location. In embodiments, the portable electronic device may include: a housing operable to encase one or more components of the portable electronic device, a power source, a plurality of light emitting diodes, a communication portal electrically coupled to the power source, a distribution module electrically coupled to the power source and operatively connected to the plurality of light emitting diodes and the communication portal, and an input device.

29 Claims, 18 Drawing Sheets

SYSTEM, DEVICE, METHOD AND PROGRAM PRODUCT TO PROVIDE HEALTHCARE AT A REMOTE LOCATION

RELATED APPLICATIONS

This application claims priority to and the benefit of U.S. Provisional Patent Application No. 63/003,567, entitled SYSTEM, DEVICE, METHOD AND PROGRAM PRODUCT TO PROVIDE HEALTHCARE AT A REMOTE LOCATION and filed on Apr. 1, 2020, the contents of which are incorporated herein by reference in their entirety.

FIELD

The present invention generally relates to technological improvements in devices, systems, methods, and program products used to provide healthcare in non-traditional environments, such as in a hallway of an overcrowded hospital or in a pop-up hospital. In exemplary embodiments, the invention relates to new technology enabling healthcare providers to monitor the health and address health emergencies associated with patients outside of a typical hospital setting.

BACKGROUND

Global pandemics, including COVID-19, have highlighted a lack of space and supplies available to medical and healthcare providers. As hospitals become overwhelmed, patients are either treated remotely or outside of a typical hospital room setting. Managing patients both in and out of a typical hospital room setting presents great difficulties in administering treatment to those who need it.

With the advent of make shift hospitals and treatment centers, there is suddenly a technological challenge in providing hospital quality treatment in make shift spaces. Current equipment is not made to be portable, monitor, and communicate with patients, monitoring devices, and caregivers. When moved off-site, current equipment present technical challenges with regards to operating in remote environments.

Accordingly, it would be beneficial to provide a system, device, method, and program product to provide healthcare at a remote location. It would also be beneficial to provide a portable, hygienic device capable of both monitoring patients and medical devices while alerting healthcare and medical providers when their personal attention is needed.

SUMMARY

An object of the present invention is to address one or more the above technological problems outlined with respect to the prior art.

As the various exemplary embodiments discussed herein illustrate, the unique and unconventional combination of elements set forth herein overcome the technological challenges posed in treating patients in remote locations.

In embodiments, a portable electronic device may provide healthcare to a subject at a remote location. In embodiments, the portable electronic device may include: (a) a housing; (b) a power source operable to provide power to the portable electronic device; (c) a plurality of light emitting diodes electrically coupled to the power source, wherein each of the plurality of light emitting diodes is operable to selectively: i. emit one or more colors; and ii. blink, and wherein each of the plurality of light emitting diodes is positioned such that light emitted from each of the plurality of light emitting diodes is visible from outside the housing; (d) a communication portal electrically coupled to the power source, wherein at least a portion of the communication portal is located inside the housing; and (e) an input device electrically coupled to the power source and operatively connected to the plurality of light emitting diodes and the communication portal, wherein the input device is located outside the housing and is electrically coupled to the power source via an electrical cord, wherein the portable electronic device is operable to be mechanically coupled to one or more patient devices associated with the subject, wherein the portable electronic device is operable to provide a notification to one or more healthcare providers associated with the subject, and wherein the portable electronic device is configured to perform the following steps: A. receive, via the input device, an input from the subject indicating attention from the one or more healthcare providers is requested by the subject; and B. illuminate, in response to the input from the subject, one or more of the plurality of light emitting diodes.

In embodiments, the portable electronic device may further include: (f) a hook outside the housing and mechanically coupled to the housing, wherein the hook is operable to be mechanically coupled to the one or more patient devices.

In embodiments, the one or more patient devices may include an IV for infusion.

In embodiments, the input device may include: i. a patient input device operable to receive a first one or more inputs which indicate attention from the one or more healthcare providers is requested by the subject; and ii. a healthcare provider input device operable to receive a second one or more inputs which indicate attention from the one or more healthcare providers has been provided to the subject.

In embodiments, the communication portal may include: i. an infra-red receiver operable to receive information from a nurse call station associated with the one or more healthcare providers, wherein the infra-red receiver is at least partially outside the housing; and ii. an infra-red transmitter operable to send communication to the nurse call station.

In embodiments, the communication portal may include: i. an antenna operable to receive information via radio waves from a nurse call station associated with the one or more healthcare providers, wherein the antenna is at least partially outside the housing; and ii. a radio transmitter operable to send radio frequencies to the nurse call station.

In embodiments, the portable electronic device may further include: (f) memory, positioned inside the housing and electrically coupled to the power source, the memory configured to store: i. identity information associated with the subject; and ii. medical information associated with the subject.

In embodiments, the portable electronic device may further include: (f) a computing device, at least partially inside the housing and electrically coupled to the power source, configured to: i. monitor one or more medical devices associated with the subject by receiving, from the one or more medical devices, one or more of the following: 1. medical data associated with a medical condition of the subject, wherein the medical data includes biometric information of the subject, and wherein the medical data is obtained by the one or more medical devices; 2. power data associated with a power supply of the one or more medical devices, wherein the power data indicates one or more of the following: A. whether the one or more medical devices is receiving electrical power; and B. an amount of electrical power remaining from one or more power supplies corresponding to the one or more medical devices; ii. determine whether an emergency is occurring by determining whether the medical data associated with the medical condition of the subject indicates the emergency; iii. determine whether the one or more medical devices has sufficient power based on the power data and a predetermined minimum power threshold; iv. in the event of the emergency occurring, cause one or more of the plurality of light emitting diodes to illuminate; and v. in the event one or more of the one or more medical devices does not have sufficient power, cause one or more of the plurality of light emitting diodes to illuminate.

In embodiments, the portable electronic device may be further configured to: A. in the event of the emergency occurring, send a first notification to a nurse call station associated with the one or more healthcare providers, wherein the first notification indicates the emergency is occurring; and B. in the event one or more of the one or more medical devices does not have sufficient power, send a second notification to the nurse call station indicating the one or more of the one or more medical devices does not have sufficient power.

In embodiments, the computing device may be further configured to: vi. store, in memory operatively connected to the portable electronic device, the received medical data and the received power data; vii. monitor, based on medical data received and medical data stored, health of the subject; viii. determine, based on medical data received and medical data stored, a status of the subject based on one or more of the following: 1. comparing the medical data received to typical healthy medical data; 2. comparing the medical data received to medical information associated with the subject; and 3. comparing the medical data received to medical data stored to determine a status trend associated with the subject; ix. in the event the status of the subject is a negative status, cause one or more of the plurality of light emitting diodes to illuminate in a first color, wherein the first color indicates the negative status of the subject; x. in the event the status of the subject is a positive status, cause one or more of the plurality of light emitting diodes to illuminate in a second color, wherein the second color indicates the positive status of the subject; and xi. in the event the status of the subject is a neutral status, cause one or more of the plurality of light emitting diodes to illuminate in a third color, wherein the third color indicates the neutral status of the subject.

In embodiments, the portable electronic device may be further configured to: A. send a first notification to a nurse call station associated with the one or more healthcare providers, wherein the first notification indicates the status of the subject. In embodiments, the portable electronic device is further operable to: B. in the event the status of the subject changes, send a second notification to the nurse call station indicating the status of the subject changing.

In embodiments, the portable electronic device may further include: (g) an audio output electrically coupled to the power source, wherein the audio output is configured to: i. in the event of the emergency occurring, play a first alarm; ii. in the event one or more of the one or more medical devices does not have sufficient power, play a second alarm; and iii. in the event the status of the subject is a negative status, play a third alarm.

In embodiments, the one or more medical devices may include a ventilator.

In embodiments, the one or more medical devices may include an intravenous control device.

In embodiments, the one or more medical devices may include a medication administering device.

In embodiments, the power source may include one or more disposable batteries.

In embodiments, the power source may include one or more rechargeable batteries.

In embodiments, the one or more rechargeable batteries may be charged via capacitive coupling.

In embodiments, the portable electronic device may further include: (g) an audio output electrically coupled to the power source, wherein the audio output is operable to, in response to the input from the subject, play an alarm.

In embodiments, the portable electronic device may further include: (f) one or more sensor devices electrically coupled to the power source, wherein the one or more sensor devices may include: 1. a smoke detector comprising an alarm and configured to detect smoke and fire within a predetermined radius of the subject.

In embodiments, the smoke detector may be further configured to: i. in the event of detecting smoke, activate the alarm; ii. in the event of detecting fire, activate the alarm; and iii. in the event of low battery, activate the alarm.

In embodiments, the smoke detector may be further configured to notify a nurse call station associated with the one or more healthcare providers in the event of detecting smoke, fire, or low battery.

In embodiments, the one or more patient devices may include a wheelchair.

In embodiments, the one or more patient devices may include a gurney.

In embodiments, the one or more patient devices may include a bed.

In embodiments, the one or more patient devices may include a removable pole.

In embodiments, the removable pole may include an intravenous drug delivery mechanism.

In embodiments, the portable electronic device may further include: (f) a distribution module electrically coupled between the input device and the communication portal.

In embodiments, a portable electronic device to provide healthcare to a subject at a remote location may include: (a) a housing; (b) a power source operable to provide power to the portable electronic device; (c) a plurality of light emitting diodes electrically coupled to the power source, wherein each of the plurality of light emitting diodes is operable to: i. emit one or more colors; and ii. blink, and wherein each of the plurality of light emitting diodes is positioned such that light emitted from each of the plurality of light emitting diodes is visible outside the housing; (d) a communication portal electrically coupled to the power source, wherein at least a portion of the communication portal is located inside the housing; (e) a distribution module electrically coupled to the power source and operatively connected to the plurality of light emitted diodes and the communication portal; wherein the distribution module is located outside the housing and is electrically coupled to the power source via a first electrical cord; (f) an input device electrically coupled and operatively connected to the distribution module, wherein the input device is located outside the housing and is electrically coupled to the distribution module via a second electrical cord, wherein the portable electronic device is operable to be mechanically coupled to one or more patient devices associated with the subject, wherein the portable electronic device is operable to provide a notification to one or more healthcare providers associated with the subject, and wherein the portable electronic device is configured to perform the following steps: A. receive, at the input device, an input from the subject indicating attention from the one or more healthcare providers is requested by the subject; and B. illuminate, in response to the input from the subject, one or more of the plurality of light emitting diodes.

In embodiments, the portable electronic device may further include: (g) a hook outside the housing and mechanically coupled to the housing, wherein the hook is operable to be mechanically coupled to the one or more patient devices.

In embodiments, the one or more patient devices may include an IV for infusion.

In embodiments, the input device may include: i. a patient input device configured to receive a first one or more inputs which indicate attention from the one or more healthcare providers is requested by the subject; and ii. a healthcare provider input device configured to receive a second one or more inputs which indicate attention from the one or more healthcare providers has been provided to the subject.

In embodiments, the communication portal may include: i. an infra-red receiver configured to receive communication from a nurse call station associated with the one or more healthcare providers, wherein the infra-red receiver is at least partially outside the housing; and ii. an infra-red transmitter configured to send communication to the nurse call station.

In embodiments, the communication portal may include: i. an antenna configured to receive radio frequencies from a nurse call station associated with the one or more healthcare providers, wherein the antenna is at least partially outside the housing; and ii. a radio frequency transmitted configured to send radio frequencies to the nurse call station.

In embodiments, the portable electronic device may further include: (g) memory, inside the housing and electrically coupled to the power source, configured to store: i. identity information associated with the subject; and ii. medical information associated with the subject.

In embodiments, the portable electronic device may further include: (g) a computing device, at least partially inside the housing and electrically coupled to the power source, configured to: i. monitor one or more medical devices associated with the subject by receiving, from the one or more medical devices, one or more of the following: 1. medical data associated with a medical condition of the subject, wherein the medical data includes biometric information of the subject, and wherein the medical data is obtained by the one or more medical devices; 2. power data associated with a power supply of the one or more medical devices, wherein the power data indicate one or more of the following: A. whether the one or more medical devices is receiving electrical power; and B. an amount of electrical power remaining from one or more power supplies corresponding to the one or more medical devices; ii. determine whether an emergency is occurring by determining whether the medical data associated with the medical condition of the subject indicates the emergency; iii. determine whether the one or more medical devices has sufficient power by comparing the power data to a predetermined amount; in the event of the emergency occurring, cause one or more of the plurality of light emitting diodes to illuminate; and v. in the event one or more of the one or more medical devices does not have sufficient power, cause one or more of the plurality of light emitting diodes to illuminate.

In embodiments, the portable electronic device may be further configured to: A. in the event of the emergency occurring, send a first notification to a nurse call station associated with the one or more healthcare providers, wherein the first notification indicates the emergency is occurring; and B. in the event one or more of the one or more medical devices does not have sufficient power, send a second notification to the nurse call station indicating the one or more of the one or more medical devices not having sufficient power.

In embodiments, the computing device may be further configured to: vi. store, in memory operatively connected to the portable electronic device, the received medical data and the received power data; vii. monitor, based on medical data received and medical data stored, a status of the subject; viii. determine, based on medical data received and medical data stored, the status of the subject based on one or more of the following: 1. comparing the medical data received to typical healthy medical data; 2. comparing the medical data received to medical information associated with the subject; and 3. comparing the medical data received to medical data stored to determine a status trend associated with the subject; ix. in the event the status of the subject is a negative status, cause one or more of the plurality of light emitting diodes to illuminate in a first color, wherein the first color indicates the negative status of the subject; x. in the event the status of the subject is a positive status, cause one or more of the plurality of light emitting diodes to illuminate in a second color, wherein the second color indicates the positive status of the subject; and xi. in the event the status of the subject is a neutral status, cause one or more of the plurality of light emitting diodes to illuminate in a third color, wherein the third color indicates the neutral status of the subject.

In embodiments, the portable electronic device may be further configured to: A. send a first notification to a nurse call station associated with the one or more healthcare providers, wherein the first notification indicates the status of the subject.

In embodiments, the portable electronic device may be further configured to: B. in the event the status of the subject changes, send a second notification to the nurse call station indicating the status of the subject changing.

In embodiments, the portable electronic device may further include: (h) an audio output electrically coupled to the power source, wherein the audio output is configured to: i. in the event of the emergency occurring, play a first alarm; ii. in the event one or more of the one or more medical devices does not have sufficient power, play a second alarm; and iii. in the event the status of the subject is a negative status, play a third alarm.

In embodiments, the one or more medical devices may include a ventilator.

In embodiments, the one or more medical devices may include an intravenous control device.

In embodiments, the one or more medical devices may include a medication administering device.

In embodiments, the power source may include one or more disposable batteries.

In embodiments, the power source may include one or more rechargeable batteries.

In embodiments, the one or more rechargeable batteries may be charged via capacitive coupling.

In embodiments, the portable electronic device may further include: (h) an audio output electrically coupled to the power source, wherein the audio output is configured to, in response to the input from the subject, play an alarm.

In embodiments, the portable electronic device may further include: (g) one or more sensor devices electrically coupled to the power source, wherein the one or more sensor devices comprises: 1. a smoke detector comprising an alarm and configured to detect smoke and fire within a predetermined radius of the subject.

In embodiments, the smoke detector may be further configured to: i. in the event of detecting smoke, activate the alarm; ii. in the event of detecting fire, activating the alarm; and iii. in the event of low battery, activate the alarm.

In embodiments, the smoke detector may be further configured to notify a nurse call station associated with the one or more healthcare providers in the event of detecting smoke, fire, or low battery.

In embodiments, the one or more patient devices may include a wheelchair.

In embodiments, the one or more patient devices may include a gurney.

In embodiments, the one or more patient devices may include a bed.

In embodiments, the one or more patient devices may include a removable pole.

In embodiments, the removable pole may include an intravenous drug delivery mechanism.

BRIEF DESCRIPTION OF THE DRAWINGS

The above and related objects, features, and advantages of the present invention, will be more fully understood by reference to the following detailed description of the exemplary embodiments of the present invention, when taken in conjunction with the following exemplary figures, wherein.

DETAILED DESCRIPTION OF THE EMBODIMENTS

The invention generally relates to various technological improvements in devices, systems, methods, and program products used to provide healthcare in remote or nontraditional locations, such as in a hallway of an overcrowded hospital or in a pop-up hospital. In exemplary embodiments, the invention relates generally to new technology enabling healthcare providers to monitor the health and address health emergencies associated with patients outside of a typical hospital room setting.

The following description is presented to enable a person of ordinary skill in the art to make and use the invention, and is provided in the context of particular applications and their requirements. Various modifications to the embodiments will be readily apparent to those skilled in the art, and the generic principles defined herein may be applied to other embodiments and applications without departing from the spirit and scope of the invention. In the following description, numerous details are set forth for the purpose of explanation. However, one of ordinary skill in the art will realize that the invention may be practiced without the use of these specific details. In other instances, well-known structures and devices are shown in block diagram form in order not to obscure the description of the invention with unnecessary detail. Thus, the present invention is not intended to be limited to the embodiments shown, but is to be accorded the widest scope consistent with the principles and features disclosed herein.

Figure 1:
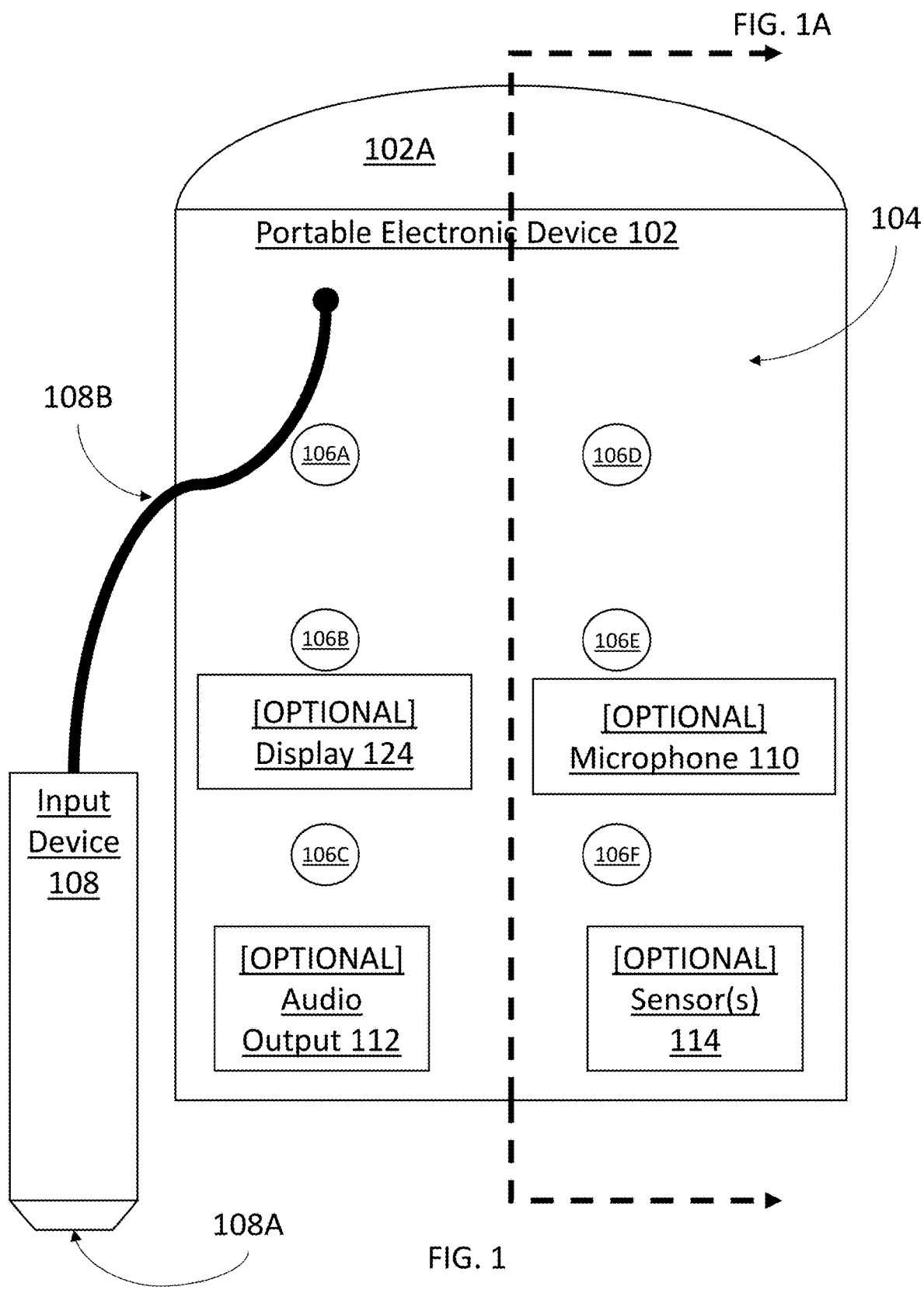
FIG. 1 is a schematic block diagram of a portable electronic device to provide healthcare to a subject at a remote location in accordance with exemplary embodiments of the present invention.

FIG. 1 is a schematic block diagram of a portable electronic device to provide healthcare to a subject at a remote location in accordance with exemplary embodiments of the present invention. The portable electronic device 102, enables healthcare providers (e.g. nurses, doctors, medical technicians, a physical therapist, to name a few) to be aware of the status of multiple patients outside of a typical hospital room setting, while being able to address patients requiring their attention. As described in more detail below, the portable electronic device 102 may receive inputs (e.g. by pushing a button, and/or audio, to name a few) from a subject (e.g. patient) and/or one or more medical devices associated with the subject (e.g. ventilator, medication pump, IV drip, to name a few) and relay that information to healthcare providers, enabling the healthcare providers to know the status of the subject and/or corresponding medical devices, as well as enabling the healthcare providers to know whether the subject is requesting and/or requires the attention of the healthcare provider. In embodiments, the portable electronic device 102 may be operatively connected (e.g. over a network) to a nurse call system (e.g. a nurse triage system), such that the inputs received by the portable electronic device 102 may be communicated to the nurse call system. In embodiments, the nurse call system may be in a hospital that is servicing the remote location. In embodiments, the remote location may refer to one or more of the following: a parking lot, a stadium, a park, the hallway of a hospital, and/or a building, to name a few.

Figure 1A:
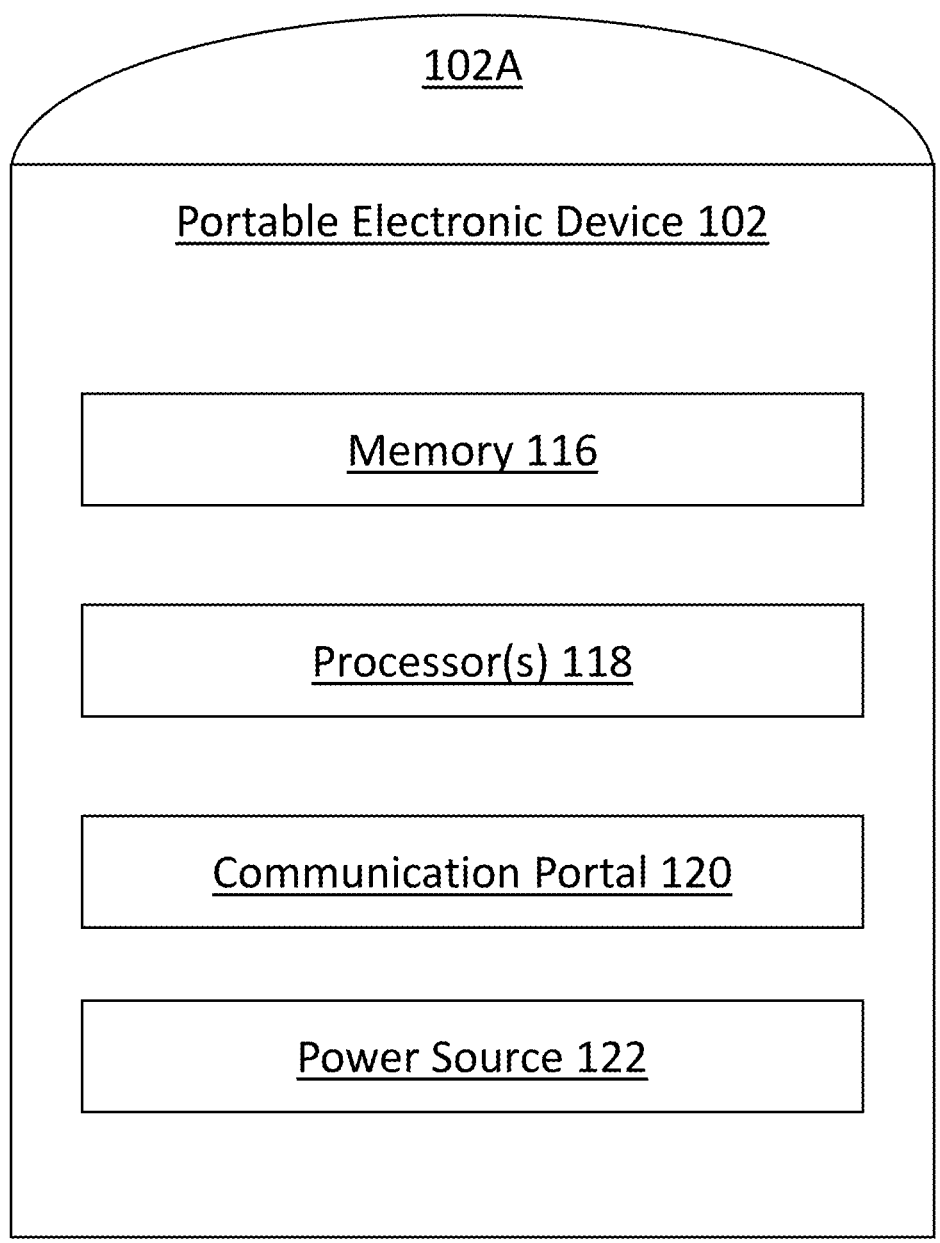
FIG. 1A is a cross-section view of the portable electronic device of FIG. 1 in accordance with exemplary embodiments of the present invention.
Figure 1B:
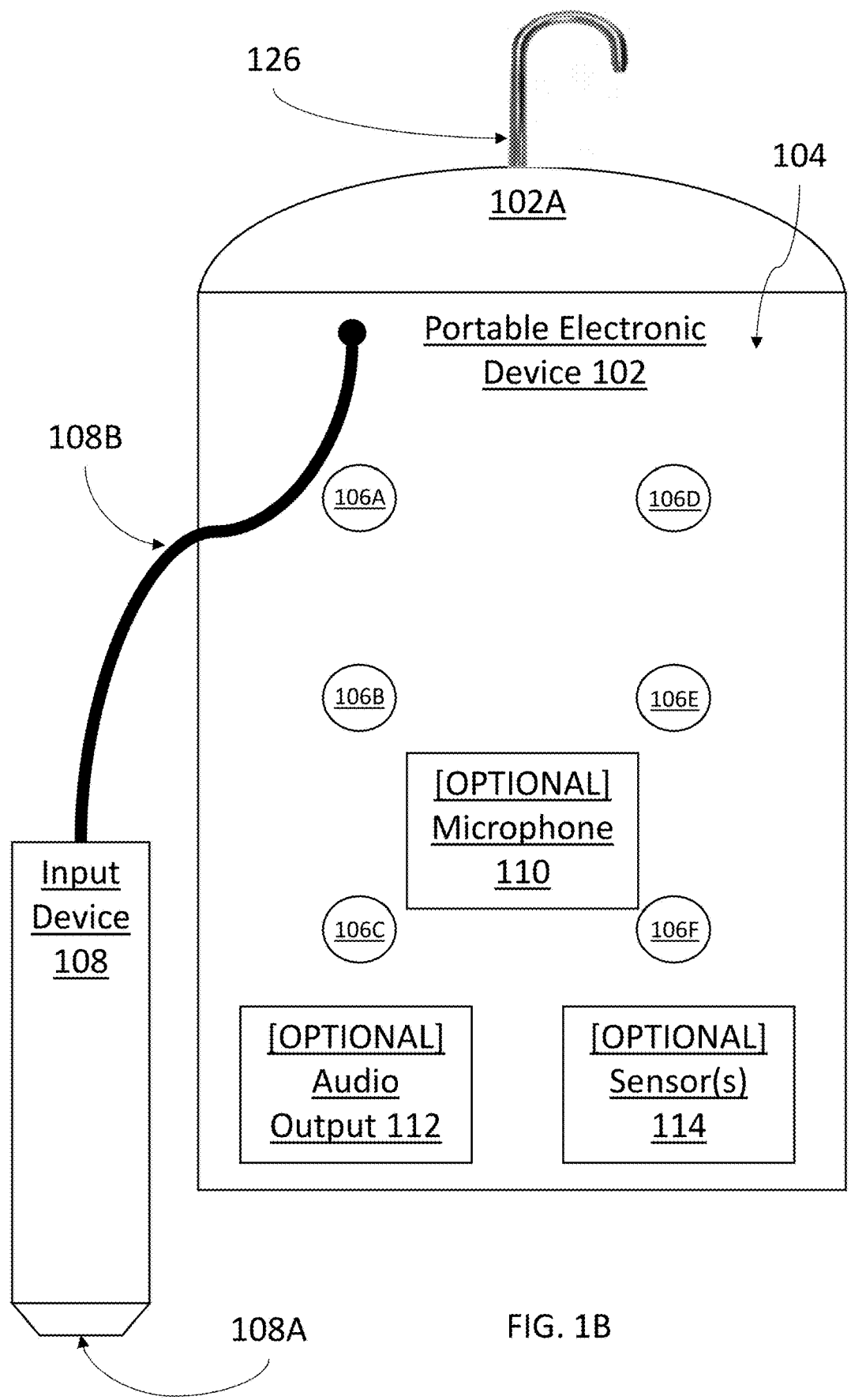
FIG. 1B is a schematic block diagram of a portable electronic device to provide healthcare to a subject at a remote location with a hook in accordance with exemplary embodiments of the present invention.
Figure 1C:
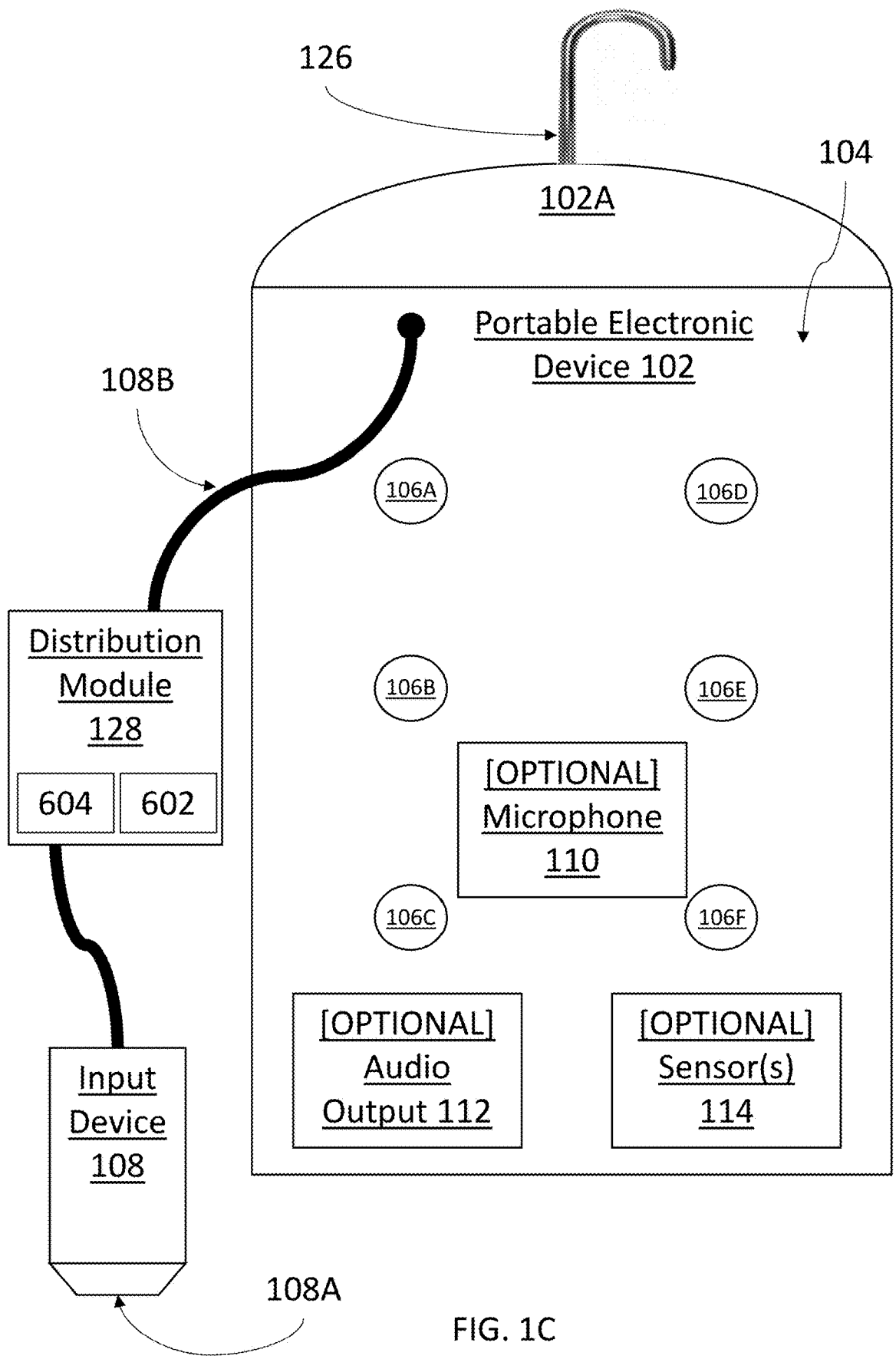
FIG. 1C is a schematic block diagram of a portable electronic device to provide healthcare to a subject at a remote location with a hook in accordance with exemplary embodiments of the present invention.

In exemplary embodiments, as shown in FIGS. 1, 1A, and 1B, the portable electronic device 102 may include one or more of the following: an LED Module 102A, a housing 104, one or more light emitting diodes 106A, 106B, 106C, 106D, 106E, and 106F (hereinafter "LED(s) 106"), an input device 108, microphone 110, audio output 112, sensor(s) 114, memory 116, processor(s) 118, communication portal 120, power source 122, display 124, and/or hook 126, to name a few. In exemplary embodiments, as shown in FIG. 1C, the portable electronic device 102 may further include an intermediary distribution module 128 having one or more input device jacks 604 and a main module jack 602. In embodiments, the housing 104 may include one or more components of the portable electronic device 102 (as shown in connection with FIG. 1A). The housing 104, in embodiments, may be water proof and/or water resistant, such that cleaning the portable electronic device 102 with water, soap, and/or bleach does not negatively affect the functionality of the portable electronic device. In embodiments, the housing 104 may be made of one or more of the following: polyethylene terephthalate, high-density polyethylene, polyvinyl chloride, low-density polyethylene, polypropylene, polystyrene, and/or a combination thereof, to name a few. The housing 104 exterior, in embodiments, may include: one or more audio jacks, one or more auxiliary inputs (e.g. where the input device 108 connects to the power source 122 via cord 108B), LED(s) 106, microphone 110, audio output 112, and/or sensor(s) 114, to name a few.

LED(s) 106, in embodiments, may refer to one or more types of light emitting diodes, including, but not limited to: miniature LEDS, decorative lights, LED floodlights, and/or LED downlights, to name a few. Each of the LED(s) 106, in embodiments, may display one or more colors. In embodiments, each of the LED(s) 106 may blink and/or be steady. In embodiments, each of the LED(s) may display a different color. The LED(s) 106, in embodiments, may illuminate in a pattern and/or individually (with the same and/or different colors, blinking at the same and/or at a different pace, and/or steady, to name a few). Different colors and/or different blinking patterns, in embodiments, may indicate to a healthcare provider, one or more of the following: the status of the subject, whether the subject has requested attention, whether the subject is experiencing an emergency, whether the portable electronic device 102 detects an emergency (e.g. via sensor(s) 114 and/or monitoring corresponding medical devices, to name a few), whether the portable electronic device 102 has a low battery, the amount of power left in the power source 122, and/or the status of associated medical devices, to name a few. In embodiments, the LED(s) may assist in triage management.

In embodiments, the visibility of LED(s) 106 may be enhanced by LED module 102A. For example, if the subject presses button 108A of the input device 108—indicating attention from a healthcare provider is requested, lighting within LED module 102A and/or LED(s) 106 may illuminate, causing the LED module 102A to illuminate the color and/or blinking of the illuminated lights. LED module 102A, in embodiments, may be mechanically coupled to the housing 104. In embodiments, the LED module 102A may be made of a translucent material that is water proof and/or water resistant. In embodiments, the LED module 102A may include one or more of the following: one or more additional light emitting diodes (that may mirror the lighting of LED(s) 106 and/or provide additional lighting or different lighting), incandescent lightbulbs, florescent lightbulbs, compact fluorescent lightbulbs, and/or halogen lamps, to name a few.

Input device 108, in embodiments, may be electrically coupled to power source 122 via cord 108B and the auxiliary jack on housing 104. In embodiments, input device 108 may include a physical input (e.g. button 108A), which, when activated (e.g. pressed), may provide a request for attention from the healthcare provider. In embodiments, input device 108 may include one or more input devices. For example, input device 108 may include a patient input device and a healthcare provider input device to ensure the healthcare provider does not come into contact with surfaces the subject has touched. Continuing the example, the healthcare input device may also include a physical input (e.g. a button), which, when activated turns off the request for attention. Although button 108A is shown as the physical input, it is understood that other physical inputs are also available and suitable for use, such as a switch, slider, and/or a touchscreen. In embodiments, the input device 108 may not include a physical input, instead requiring an input not associated with physical contact (e.g. audio input and/or sensors to detect movement or change in lighting, to name a few).

As mentioned above, in embodiments audio inputs may be received by the portable electronic device 102. For example, the portable electronic device 102 may include one or more microphone(s) (e.g. optionally included microphone 110) that receive audio inputs that cause the portable electronic device 102 to illuminate one or more of the LED(s) 106 and/or play an alarm via the audio output 112. Furthermore, the healthcare provider, in embodiments, may be able to turn the request for attention off via an audio input. Microphone 110, in embodiments, may be a transducer and/or any suitable component capable of detecting audio signals. For example, microphone 110 may include one or more sensors for generating electrical signals and circuitry capable of processing the generated electrical signals. In some embodiments, microphone 110 may include multiple microphones capable of detecting various frequency levels. As an illustrative example, portable electronic device 102 may include multiple microphones (e.g., four, seven, ten, etc.) placed at various positions about the portable electronic device 102 to monitor/capture any audio outputted in the environment the portable electronic device 102 is located. The various microphones 110 may include some microphones optimized for distant sounds, while some microphones may be optimized for sounds occurring within a close range of the portable electronic device 102. In embodiments, one or more microphone(s) 110 may serve as input devices to receive audio inputs, such as speech from the subject.

As mentioned above, in embodiments, the portable electronic device 102 may optionally include audio output 112.

Audio output 112 (e.g. speaker(s)), in embodiments, may correspond to any suitable mechanism for outputting audio. For example, audio output 112 may include one or more speaker units, transducers, arrays of speakers, and/or arrays of transducers that may be capable of broadcasting audio and or audio content to a surrounding area where the portable electronic device 102 may be located. In some embodiments, audio output 112 may include headphones or ear buds, which may be wirelessly connected, or hard-wired, to the portable electronic device 102, that may be capable of broadcasting audio directly to the subject. In some embodiments, portable electronic device 102 may be hard-wired, or wirelessly connected, to the audio output 112. For example, the portable electronic device 102 may cause the audio output 112 to output audio thereon. Continuing the example, the portable electronic device 102 may obtain audio content to be output by audio output 112, and the portable electronic device 102 may send the audio to the audio output 112 using one or more communications protocols described herein. For instance, the audio output 112 and the portable electronic device 102 may communicate with one another using a Bluetooth® connection, or another near-field communications protocol. In some embodiments, the portable electronic device 102 may communicate with the audio output 112 indirectly.

In embodiments, portable electronic device 102 may optionally include one or more sensor(s) 114. In embodiments, the one or more sensor(s) 114 may be electrically coupled to the power source 122. The one or more sensor(s) 114, may include one or more of the following: a smoke detector, a fire sensor, a temperature sensor, a location sensor, and/or a carbon monoxide sensor, to name a few. For example, the sensor(s) 114 may include a smoke detector, that, when smoke is detected near the portable electronic device 102, the portable electronic device 102 may cause the LED(s) 106 to illuminate and/or an alarm to be played by audio output 112. As another example, if the ambient temperature is above a predetermined threshold, the portable electronic device 102 may cause the LED(s) 106 to illuminate and/or an alarm to be played by audio output 112.

In embodiments, as mentioned above, the portable electronic device may optionally include display 124. Display 124, in embodiments, may be a display screen and/or touch screen, which may be any size and/or shape. In embodiments, display 124 may be a component of the portable electronic device 102 and may be located at any portion of the portable electronic device 102. Various types of displays may include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof, to name a few. The display 124 and the portable electronic device 102 may be separate devices in some embodiments, or may be combined into a single device in some embodiments. In embodiments, the display 124 may be a touch screen, which, in embodiments, may correspond to a display screen including capacitive sensing panels capable of recognizing touch inputs thereon.

The housing 104, in embodiments, may encapsulate, either fully or partially, one or more components of the portable electronic device. Referring to FIG. 1A, a cross-section of FIG. 1, the housing 104 may include one or more of the following: memory 116, processor(s) 118, communication portal, and/or power source 122, to name a few. Memory 116, in embodiments, may store information associated with the subject. For example, medical and identification information may be stored in memory 116. As another example, data monitored by the portable electronic device 102, from one or more medical devices, may also be received and stored by memory 116. Memory 116 may store one or more machine-readable instructions, enabling the portable electronic device 102 to illuminate light and play sounds in accordance with a predefined key (e.g. red is emergency, green is good, to name a few). Memory 116, may include one or more types of storage mediums such as any volatile or non-volatile memory, or any removable or non-removable memory implemented in any suitable manner to store data for portable electronic device 102. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 116 may be implemented as computer-readable storage media ("CRSM"), which may be any available physical media accessible by processor 118 to execute one or more instructions stored within memory 116. In some embodiments, one or more applications (e.g., the above described software) may be run by processor(s) 118 and may be stored in memory 116.

Processor(s) 118, in embodiments, may include any suitable processing circuitry capable of controlling operations and functionality of portable electronic device 102, as well as facilitating communications between various components within portable electronic device 102. In some embodiments, processor 118 may include a central processing unit ("CPU"), a graphic processing unit ("GPU"), one or more microprocessors, a digital signal processor, or any other type of processor, or any combination thereof. In some embodiments, the functionality of processor 118 may be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, processor 118 may include its own local memory, which may store program systems, program data, and/or one or more operating systems. However, processor 118 may run an operating system ("OS") for portable electronic device 102, and/or one or more firmware applications, media applications, and/or applications resident thereon. In embodiments, processor 118 may run a local client script for reading and rendering content received from one or more websites. For example, processor 118 may run a local JavaScript client for rendering HTML or XHTML content received from a particular URL accessed by portable electronic device 102.

In embodiments, communication portal 120, may include any circuitry allowing or enabling one or more components of portable electronic device 102 to communicate with one another. Communication portal 120, in embodiments, may enable the communication between the portable electronic device 102 and one or more of the following: one or more medical devices associated with the subject, a nurse call station, an additional display, one or more microphones, a radio, and/or one or more additional devices, servers, and/or systems, to name a few. As an illustrative example, portable electronic device 102 may monitor one or more medical devices associated with the subject over a network using the communication portal 120. A non-exhaustive list of medical devices that may be monitored by the portable electronic device, includes one or more of the following: ventilators, medication pumps, IVs, heart rate monitors, blood pressure monitors, oxygen level monitors, dialysis machines, blood sugar monitors, and/or potassium monitors, to name a few. As another illustrative example, data retrieved from the portable electronic device 102 may be transmitted over a network, such as the Internet or Bluetooth®, to a nurse call station associated with the healthcare providers using any number of communications protocols. For example, the network may be accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications between portable electronic device 102 and one or more of the following: one or more components of portable electronic device 102, one or more medical devices associated with the subject, one or more nurse call stations, an additional display, one or more microphones, a radio, one or more speakers, and/or one or more additional devices, servers, and/or systems, to name a few. In embodiments, the communication portal 120 may include an antenna and a radio frequency transmitter. In embodiments, the communication portal 120 may include an infra-red transmitter and an infra-red receiver. In embodiments, portable electronic device 102 may communicate via a web browser using HTTP. Various additional communication protocols may be used to facilitate communications between portable electronic device 102 one or more components of portable electronic device 102, the display 104, the robotic upper limb device 106, one or more microphones and/or with one or more additional devices, servers, and/or systems, to name a few, include the following non-exhaustive list, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS 136/TDMA, iDen, LTE or any other suitable cellular network protocol), optical, Bit-Torrent, FTP, RTP, RTSP, SSH, and/or VOIP.

In embodiments, communication portal 120 may use any communications protocol, such as any of the previously mentioned exemplary communications protocols. In some embodiments, portable electronic device 102 may include one or more antennas to facilitate wireless communications with a network using various wireless technologies (e.g., Wi-Fi, Bluetooth, radiofrequency, etc.). In yet another embodiment, portable electronic device 102 may include one or more universal serial bus ("USB") ports, one or more Ethernet or broadband ports, and/or any other type of hardwire access port so that communication portal 120 allows portable electronic device 102 to communicate over one or more communications networks via the network.

Figure 2A:
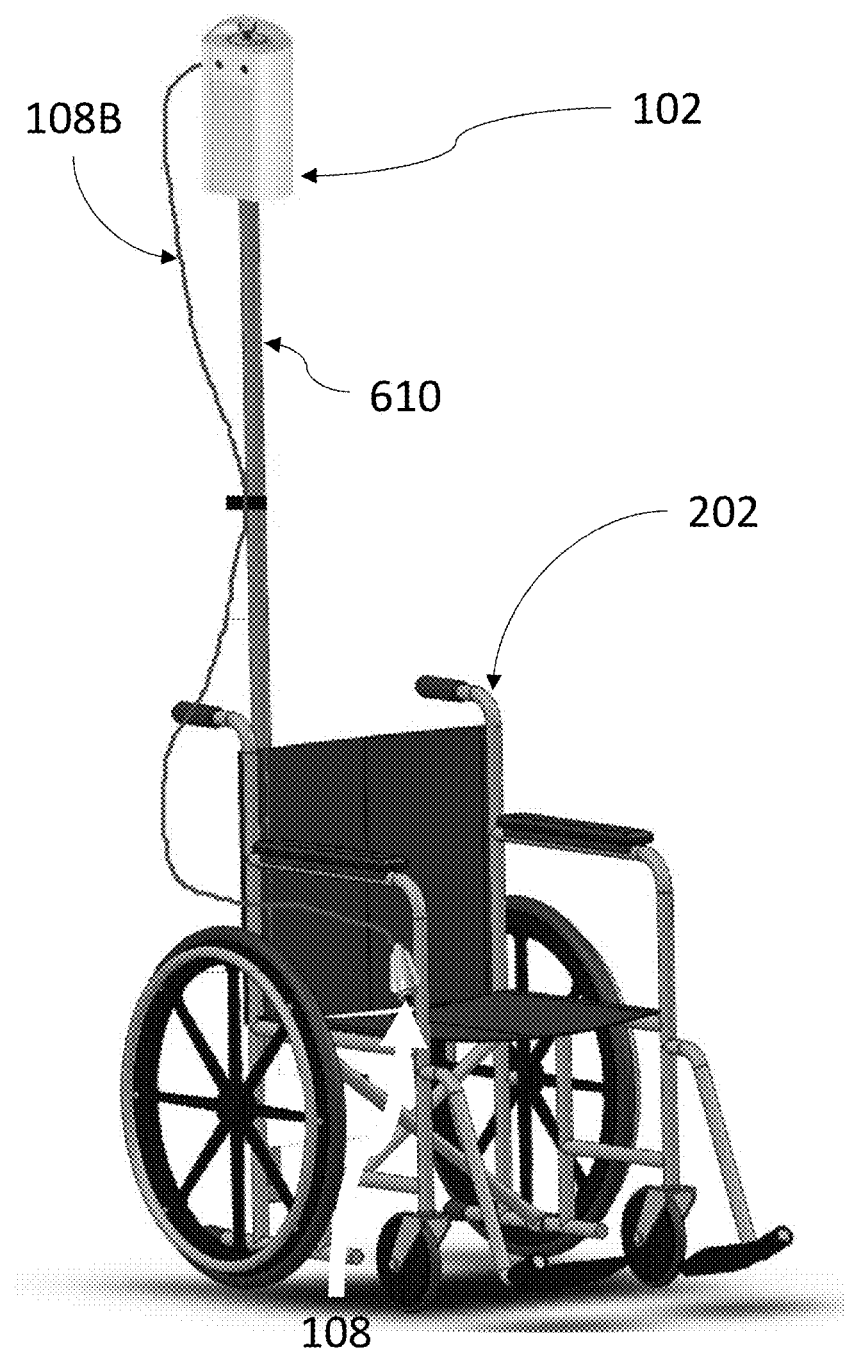
FIGS. 2A-2B are schematic block diagrams of patient devices, each of which mechanically coupled to a portable electronic device to provide healthcare to a subject at a remote location in accordance with exemplary embodiments of the present invention.
Figure 2B:
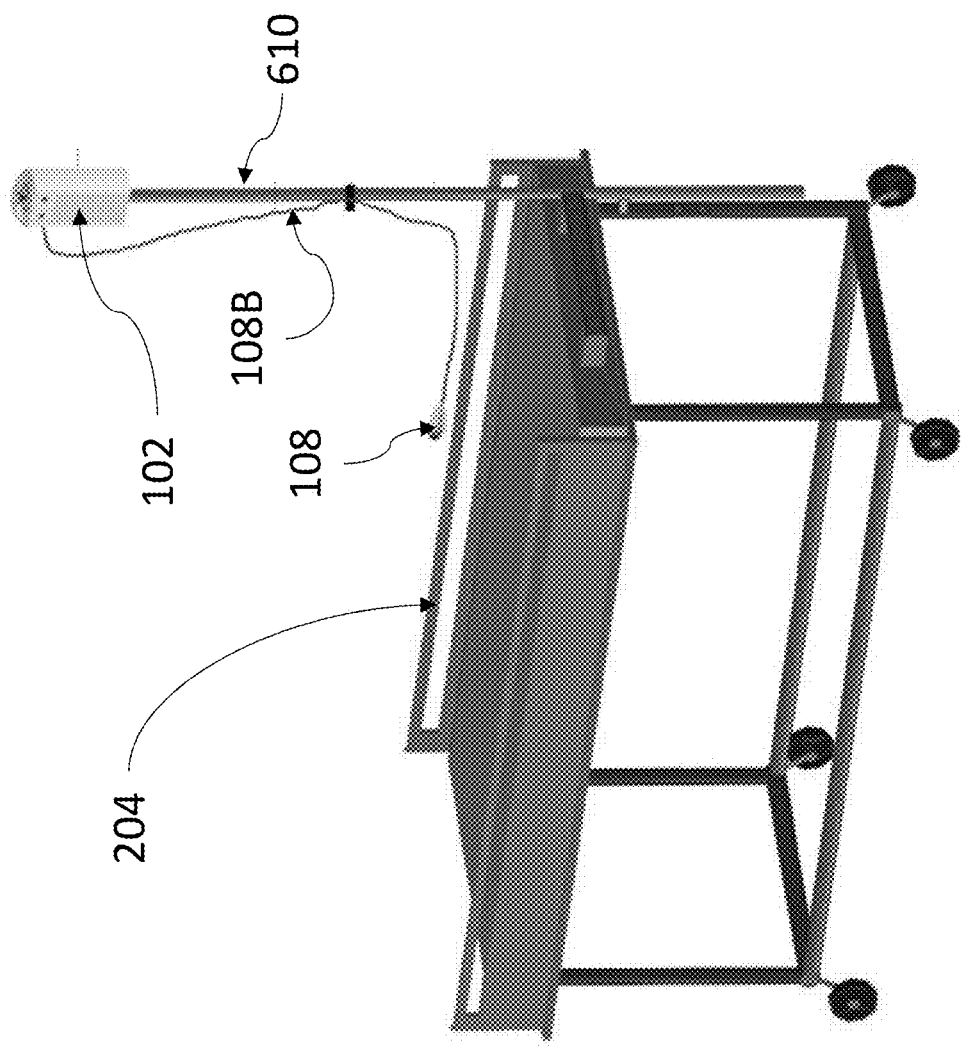

The portable electronic device 102, in embodiments, may be mechanically coupled to one or more patient devices. For example, as shown in FIG. 1B, the portable electronic device 102 may include a hook 126. The hook 126, in embodiments, may attach to an IV. Referring to FIGS. 2A and 2B, the portable electronic device 102 may be mechanically coupled to a wheelchair 202 and/or a bed 204. In embodiments, the portable electronic device may be mechanically coupled to a removable pole 610, which, in embodiments, may include an intravenous drug treatment.

Figure 4:
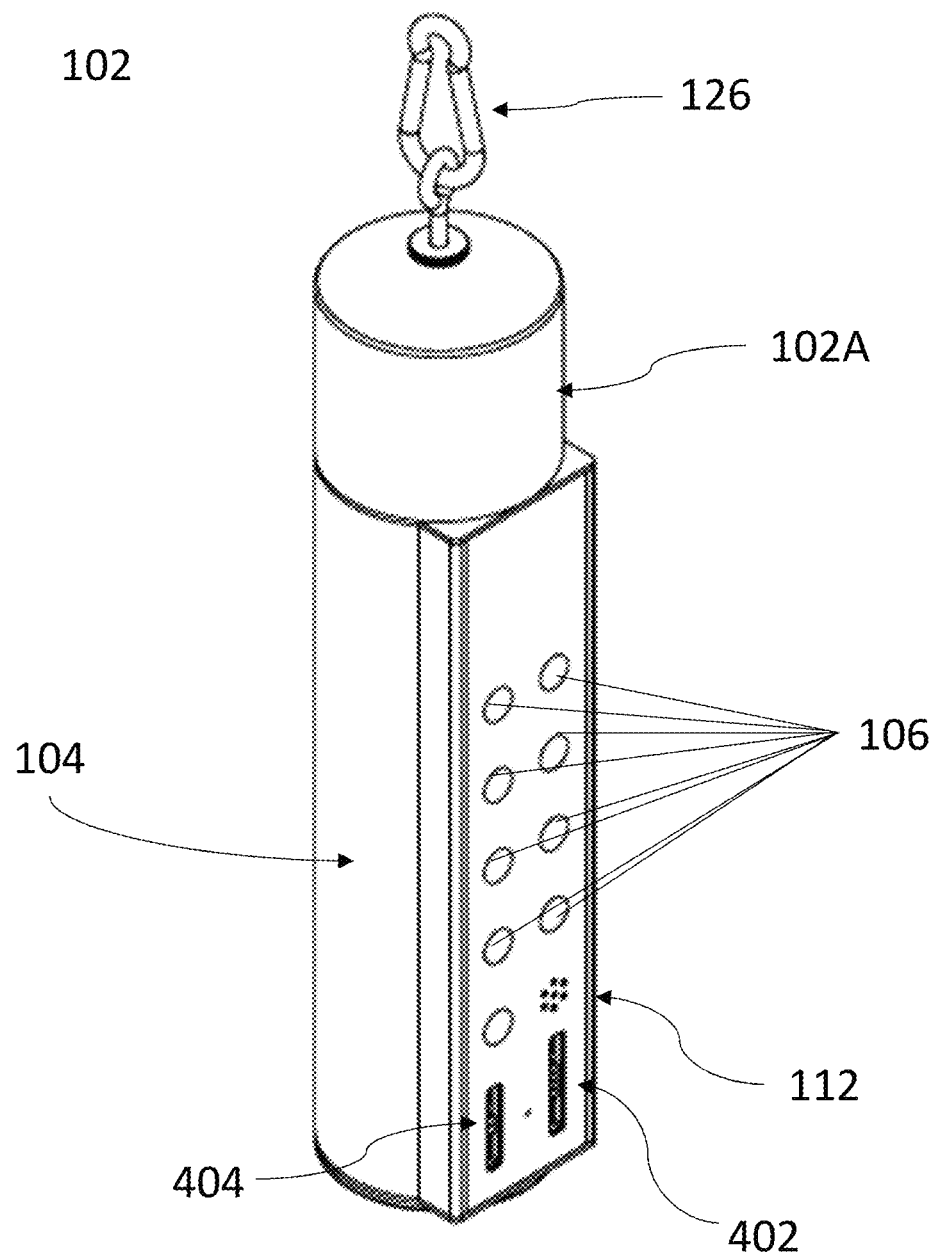
FIG. 4 is a schematic diagram of a front view of a portable electronic device to provide healthcare to a subject at a remote location with a hook in accordance with exemplary embodiments of the present invention.
Figure 4A:
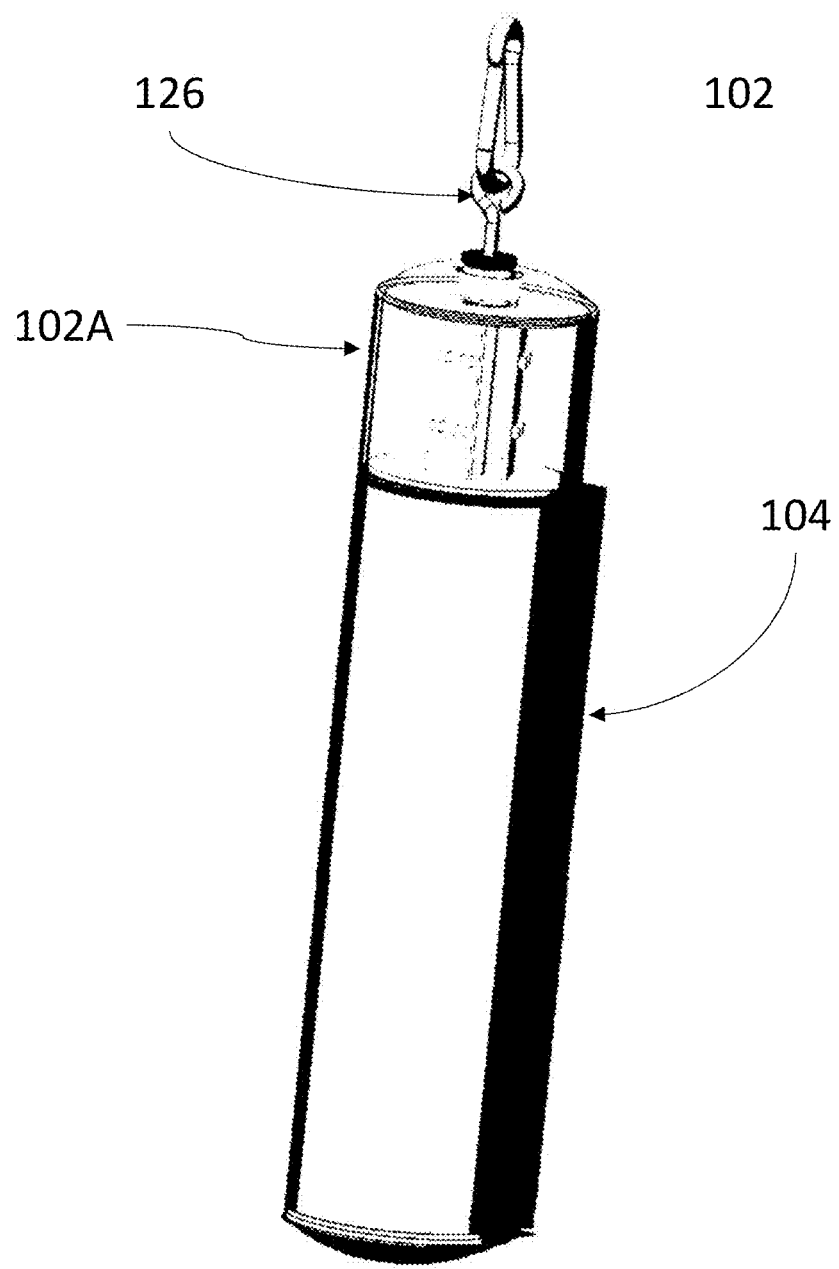
FIG. 4A is a schematic diagram of a back view of the portable electronic device of FIG. 4 to provide healthcare to a subject at a remote location with a hook in accordance with exemplary embodiments of the present invention.
Figure 4B:
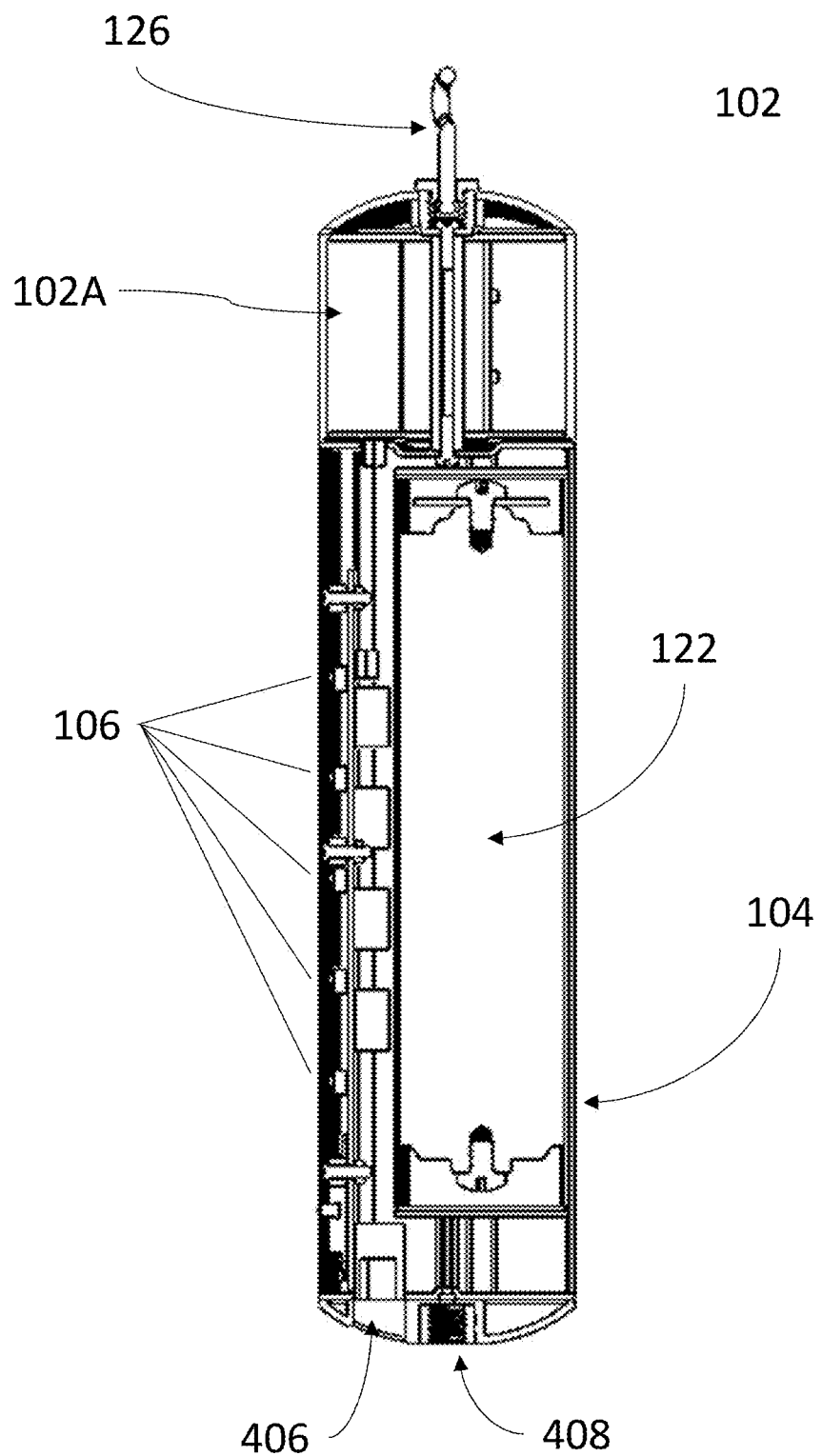
FIG. 4B is a schematic diagram of a side cross-section view of the portable electronic device of FIG. 4 to provide healthcare to a subject at a remote location with a hook in accordance with exemplary embodiments of the present invention.
Figure 4C:
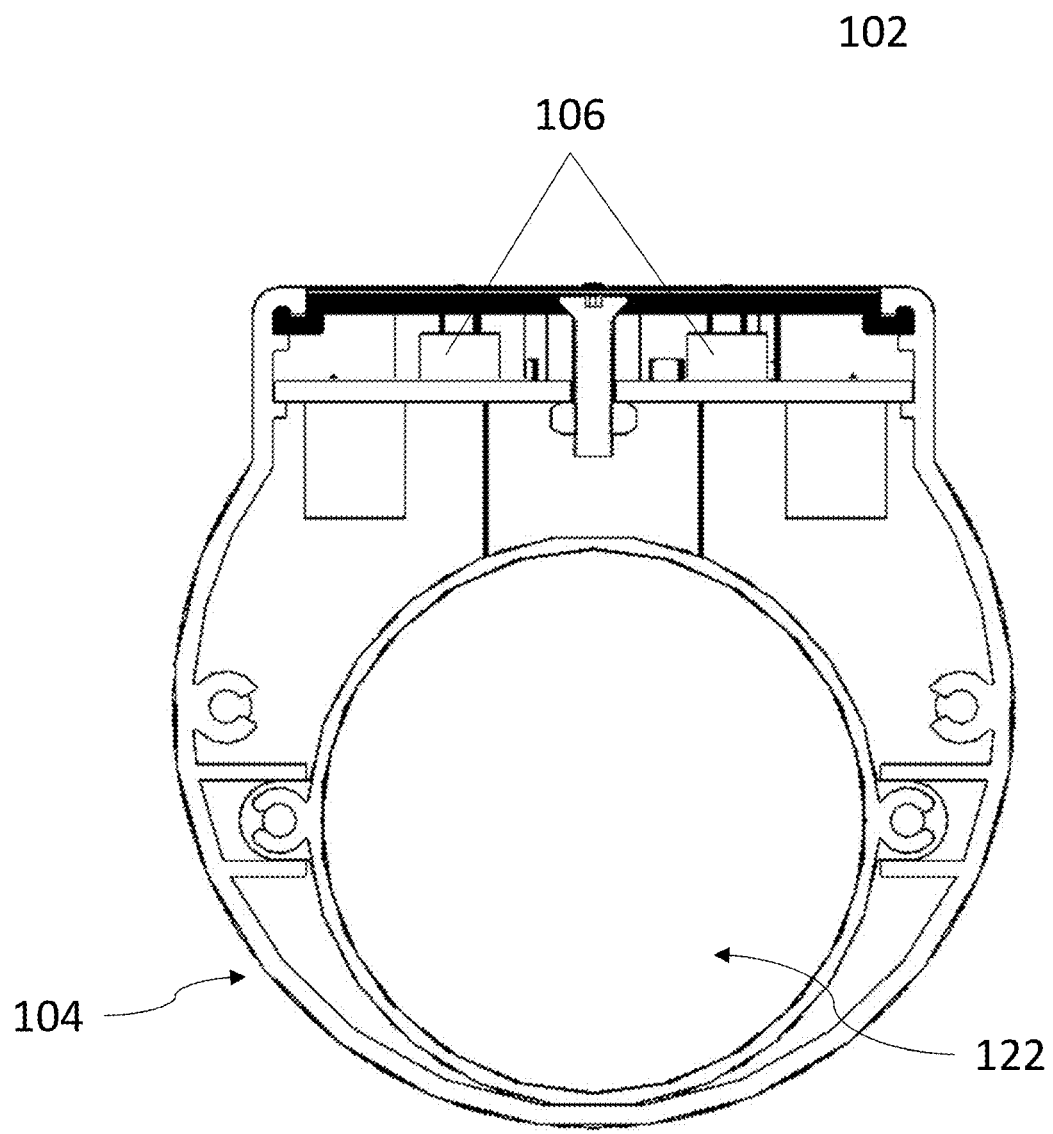
FIG. 4C is a schematic diagram of a top cross-section view of the portable electronic device of FIG. 4 to provide healthcare to a subject at a remote location with a hook in accordance with exemplary embodiments of the present invention.
Figure 4D:
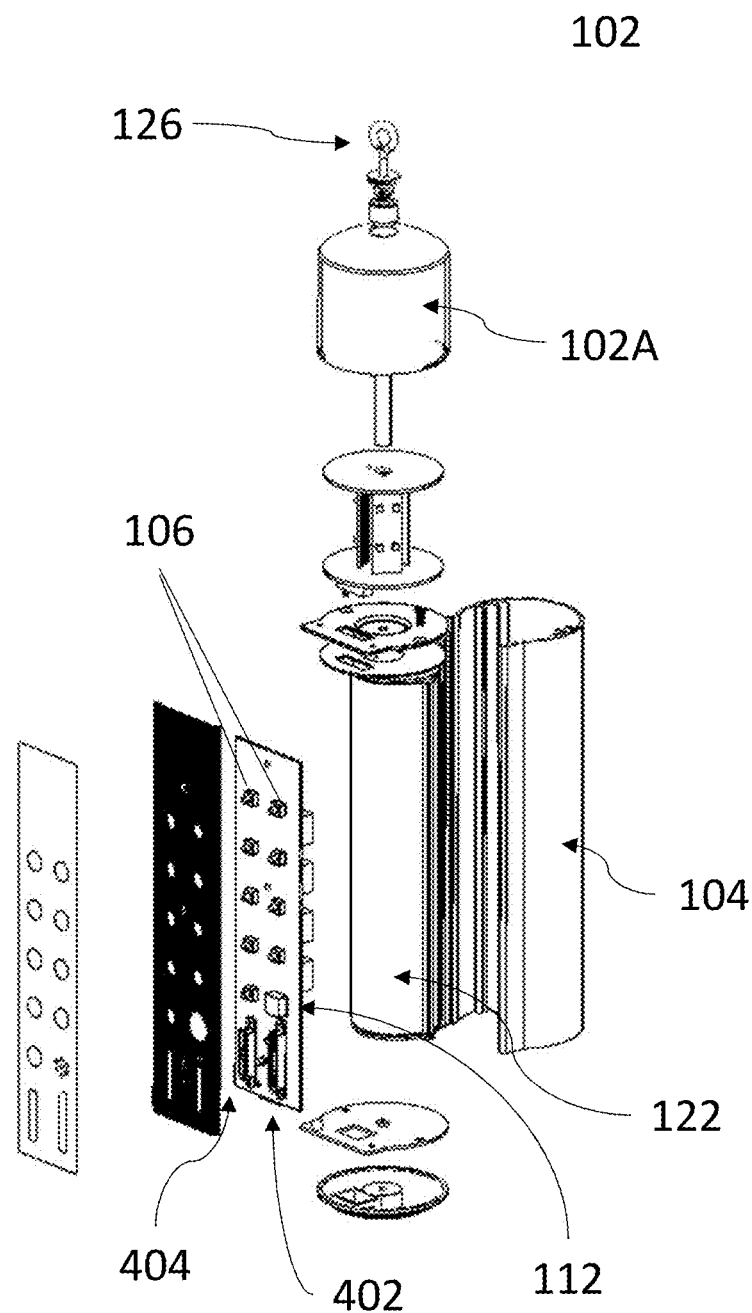
FIG. 4D is a schematic diagram of an exploded view of the portable electronic device of FIG. 4 to provide healthcare to a subject at a remote location with a hook in accordance with exemplary embodiments of the present invention.

FIG. 4 is a schematic diagram of a front view of a portable electronic device 102 to provide healthcare to a subject at a remote location with a hook 126 in accordance with exemplary embodiments of the present invention. FIG. 4D is a schematic diagram of an exploded view of the portable electronic device 102 of FIG. 4. Referring to FIGS. 4 and 4D, the portable electronic device 102 may include, in addition to the components discussed with respect to FIGS. 1-1C, a charging jack 402 and nurse call cord jack 404. In embodiments, the charging jack 402 may be used to recharge the power source 122 located inside the battery module 502 where the power source 122 is rechargeable. In embodiments, the nurse call cord jack 404 may accept a cord 108B which allows for the patient to communicate with a nurse call station and/or healthcare provider. In embodiments, the portable electronic device 102 may include a distribution module jack 406 for connecting a cord 108B to a distribution module 128. In embodiments, the portable electronic device 102 may include a threaded insert 408 to facilitate mounting the portable electronic device 102 to the removable pole 610.

Figure 6:
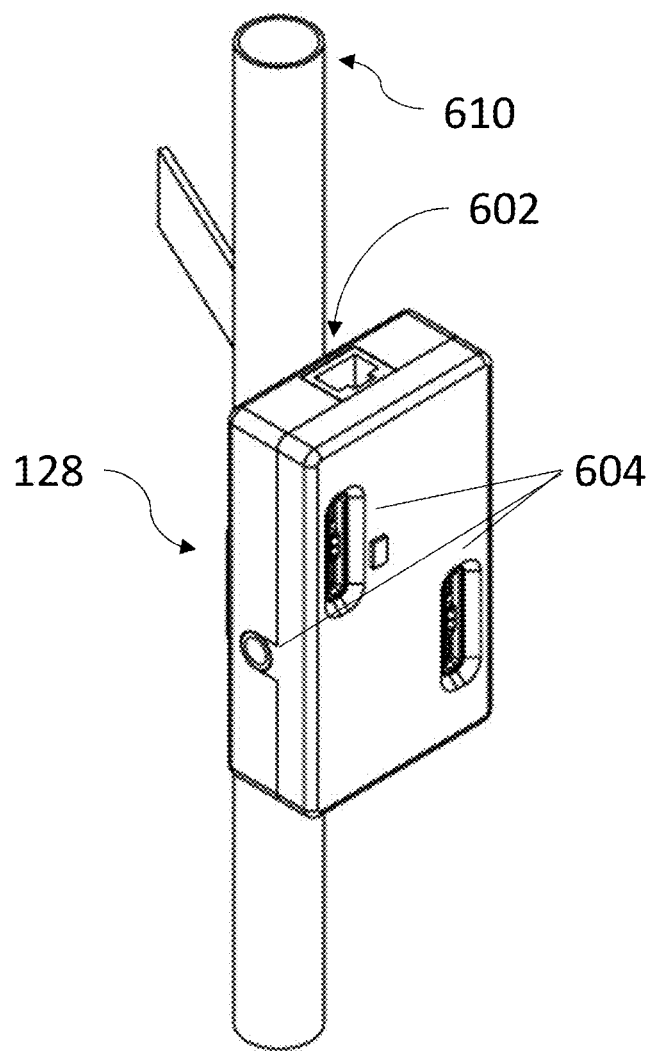
FIG. 6 is a schematic diagram of a front view of a distribution module of a portable electronic device to provide healthcare to a subject at a remote location with a hook in accordance with exemplary embodiments of the present invention.
Figure 6A:
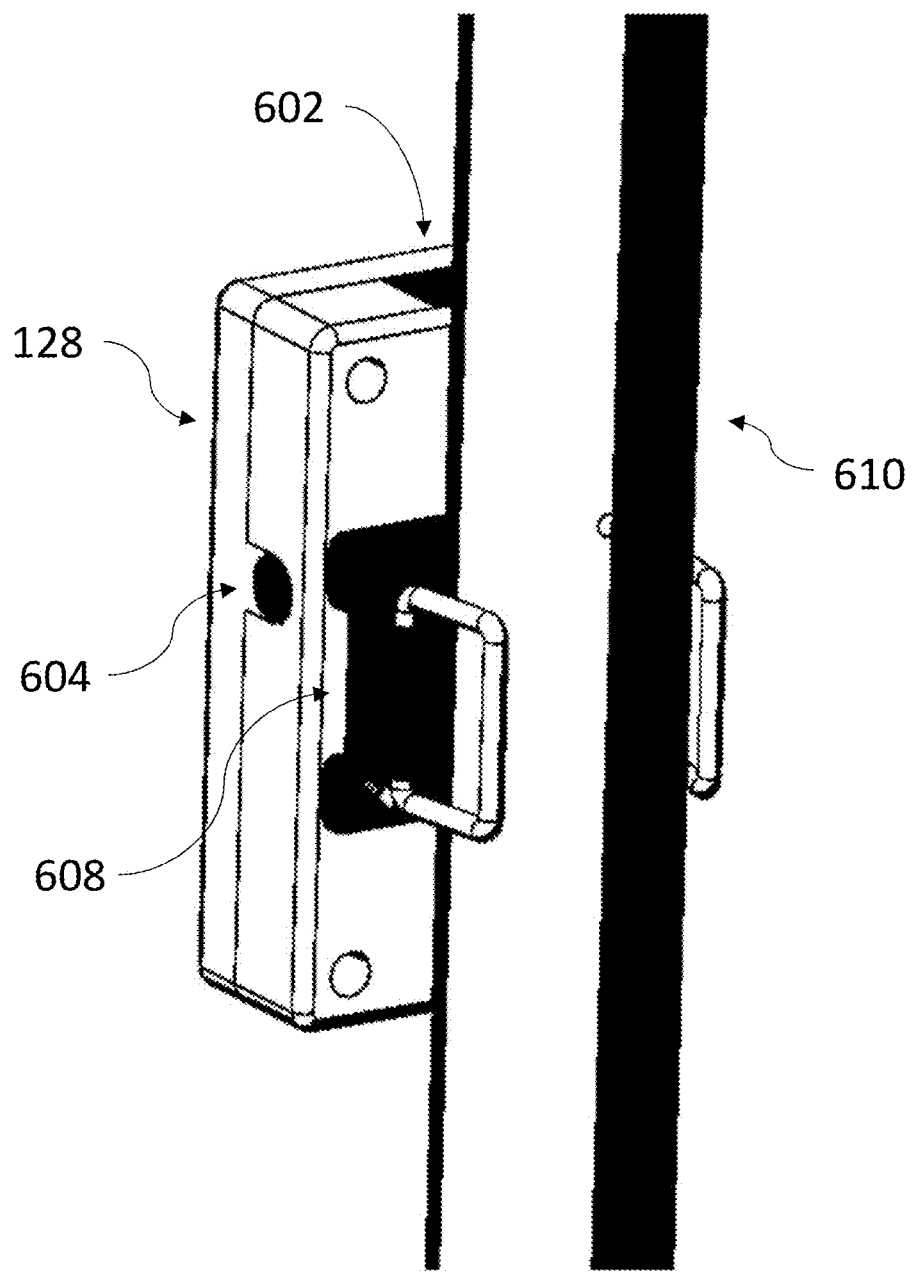
FIG. 6A is a schematic diagram of a back view of the distribution module of FIG. 6 in accordance with exemplary embodiments of the present invention.

Referring to FIG. 1C, the portable electronic device 102 of FIGS. 1-1B may include an intermediary distribution module 128 electrically coupled between the input device 108 and the communication portal 120. In embodiments, the distribution module 128 may be electrically coupled to the power source 122 of the portable electronic device 102 and may be operatively connected to the LEDs 106 and the communication portal 120. In embodiments, the distribution module 128 may be located outside the housing 104 and may be electrically coupled to the power source 122 via a cord 108B. In embodiments, as shown in FIGS. 6 and 6A, the distribution module 128 may include one or more input device jacks 604, a main module jack 602, and a mounting plate 610. In embodiments, the one or more input device jacks 604 may allow for the connection of one or more cords 108B between the distribution module 128 and an input device 108. In embodiments, the main module jack 602 may allow for the connection of a cord 108B to the portable electronic device 102. In embodiments, the mounting plate 610 may be used to mount the distribution module 128 to the removable pole 610.

Figure 2C:
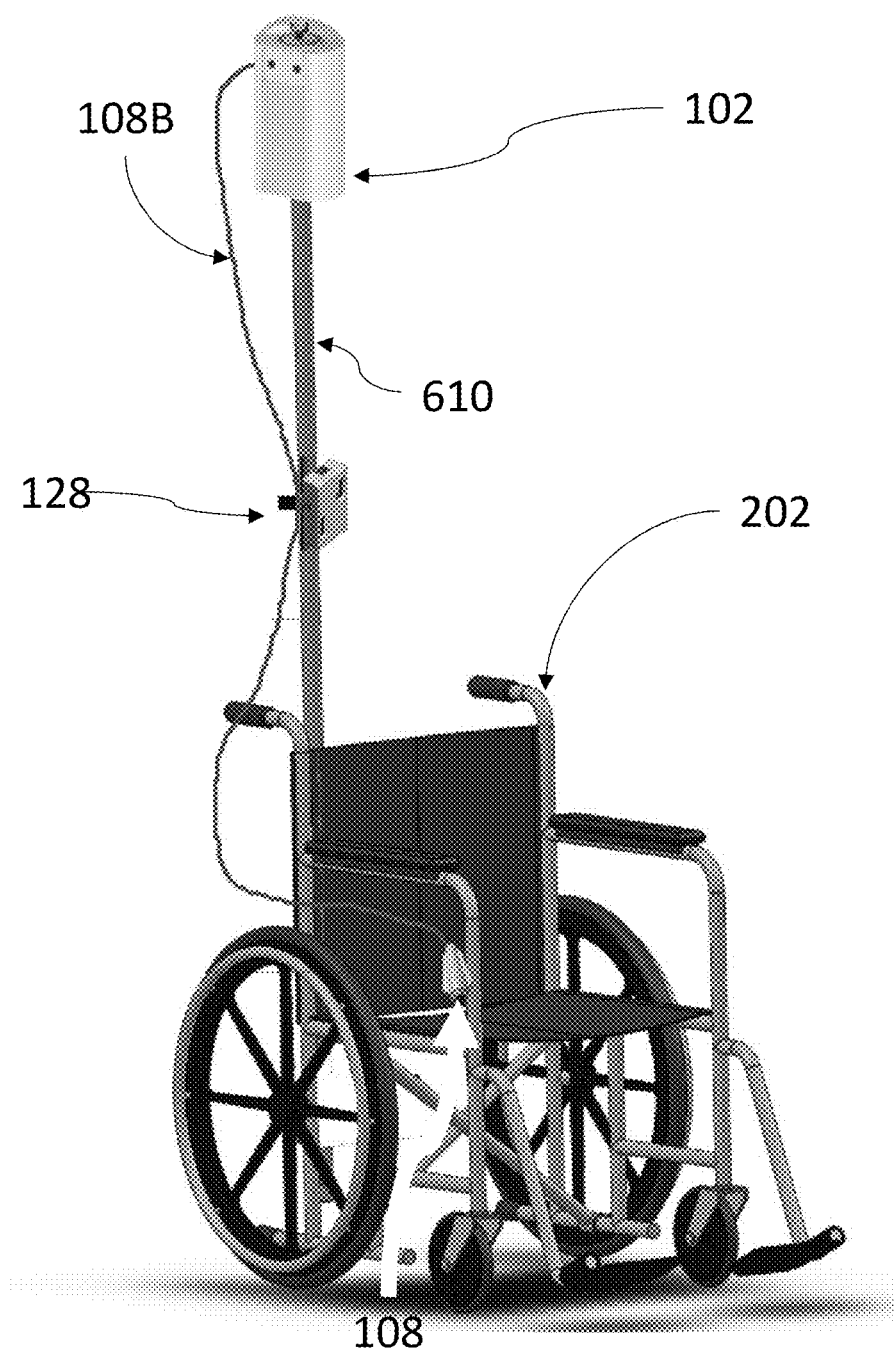
FIGS. 2C-2D are schematic block diagrams of patient devices, each of which are mechanically coupled to a portable electronic device via a distribution module to provide healthcare to a subject at a remote location in accordance with exemplary embodiments of the present invention.
Figure 2D:
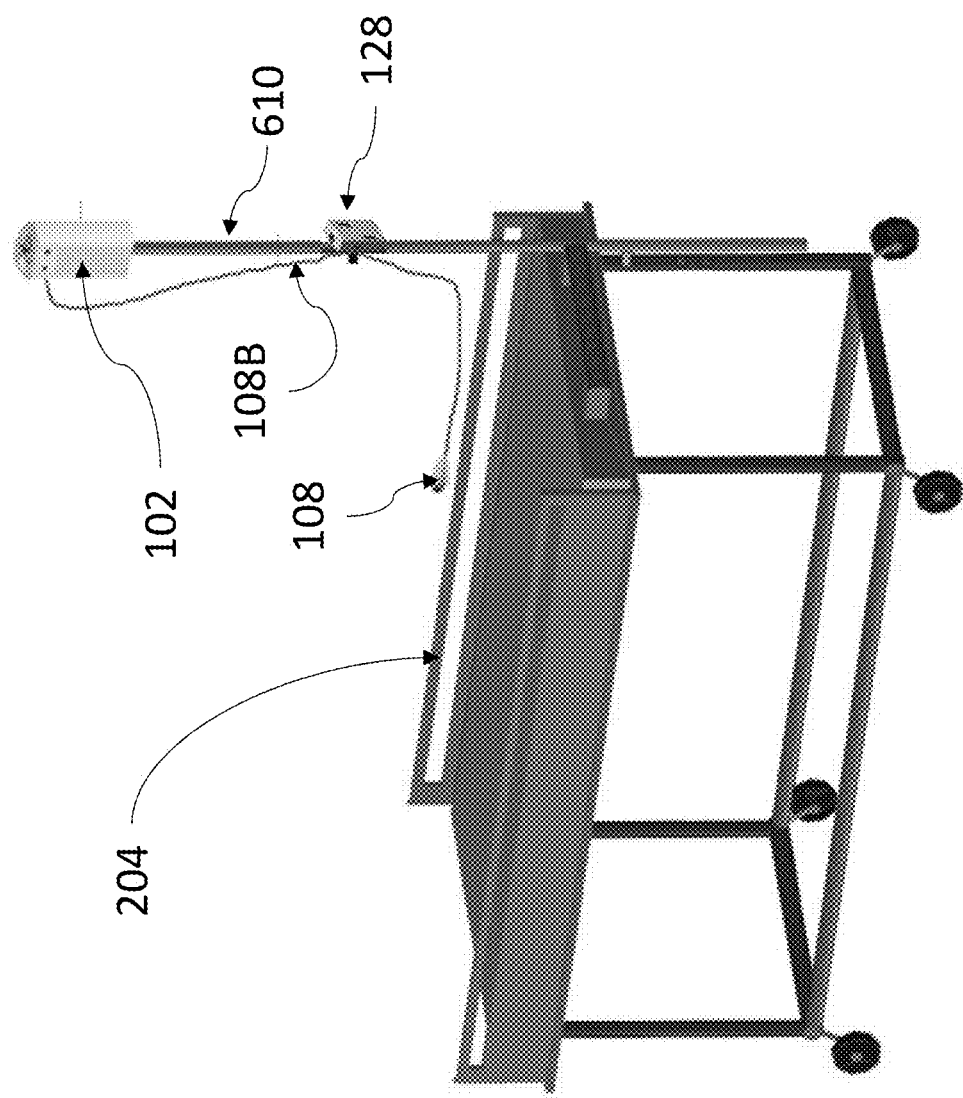

Referring to FIGS. 2C and 2D, the portable electronic device 102 may be mechanically coupled to a wheelchair 202 and/or a bed 204, and a distribution module 128. In embodiments, the input device 108 may be coupled to the communication portal 120 of the portable communication device 102 via the intermediary distribution module 128 of FIG. 1C. In embodiments, the portable electronic device 102 may be mechanically coupled to a removable pole 610, which, in embodiments, may include an intravenous drug treatment. One problem with coupling the portable electronic device 102 to the removable pole 610 for IV drug treatment is that the suspension of the portable electronic device 102 in this embodiment may cause any of the one or more cords 108B of the input device 108 to become entangled or snagged on the wheelchair 202, bed 204, or any other outside object. In embodiments, the intermediary distribution module 128 provides a technical solution to the entangled cables problem by lowering the connection point of the input device 108 so that the one or more cords 108B of the input device 108 may not interfere with the operation of the portable electronic device 102, wheelchair 202 or bed 204.

Figure 5:
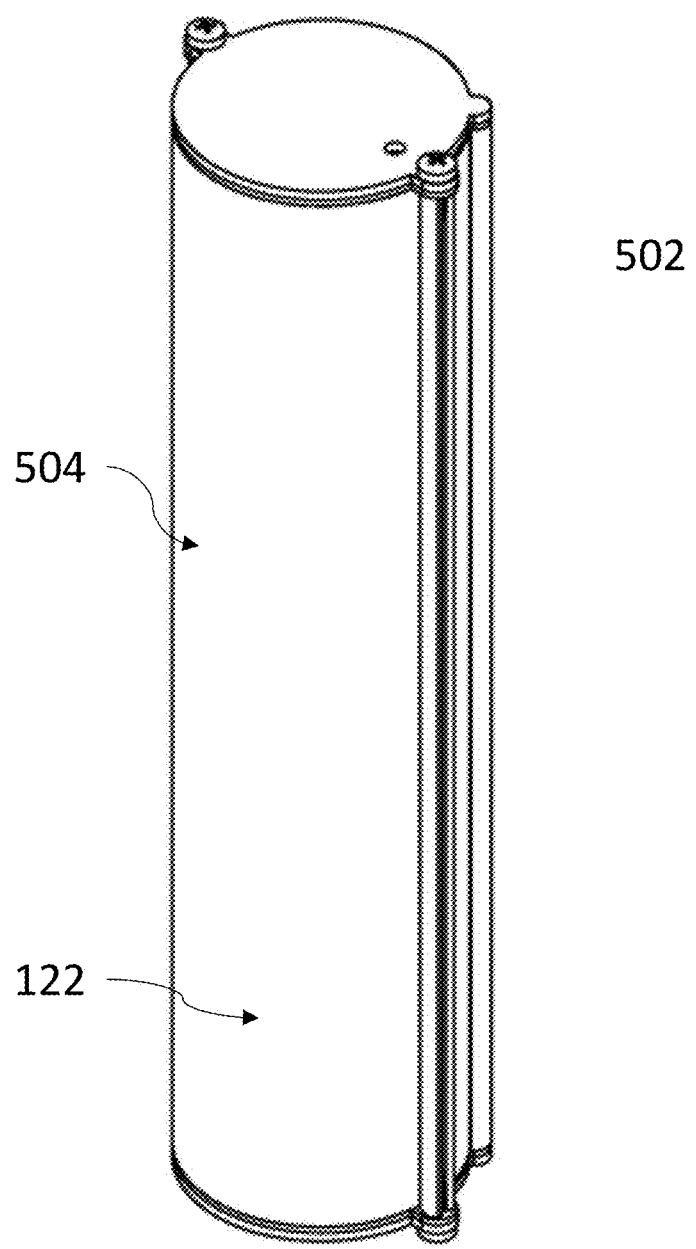
FIG. 5 is a schematic diagram of a front view of a battery module of the portable electronic device of FIG. 4 to provide healthcare to a subject at a remote location with a hook in accordance with exemplary embodiments of the present invention.

The portable electronic device 102, in embodiments, may include a power source 122. In embodiments, as shown in FIG. 5, the power source 122 may be located in a battery module 502 having a battery module housing 504. The power source 122, in embodiments, may be a port for a power source 122 to connect to. In embodiments, the power source 122 may be disposable and/or rechargeable batteries. The power source 122, in embodiments, may include one or more of the following: alkaline batteries, lithium batteries, lithium ion batteries, carbon batteries, lead-acid batteries, and/or an electro-magnetic battery, to name a few. In embodiments the power source 122, may be recharged via capacitive coupling.

The portable electronic device 102, in embodiments, as used herein, may correspond to any suitable type of mobile electronic device including, but are not limited to, desktop computers, mobile computers (e.g., laptops, ultrabooks), mobile phones, portable computing devices, such as smart phones, tablets and phablets, televisions, set top boxes, smart televisions, personal display devices, and/or personal digital assistants ("PDAs"), to name a few. In some embodiments, the portable electronic device 102 may be relatively simple or basic in structure such that no, or a minimal number of, mechanical input option(s) (e.g., keyboard, mouse, track pad) or touch input(s) (e.g., touch screen, buttons) are included. For example, the portable electronic device 102 may be able to receive and output audio, and may include power, processing capabilities, storage/memory capabilities, and communication capabilities. However, in other embodiments, the portable electronic device 102 may include one or more components for receiving mechanical inputs (e.g. via input device 108) or touch inputs, such as a touch screen and/or one or more buttons (e.g. button 108A).

In embodiments, the portable electronic device 102 may be a voice activated electronic device. A voice activated electronic device, as described herein, may correspond to any device capable of being activated in response to detection of a specific word or phrase (e.g., a word, a phoneme, a phrase or grouping of words, or any other type of sound, or any series of temporally related sounds). For example, a voice activated electronic device may be one or more of the following: Amazon Alexa-enabled devices, Amazon Echo®; Amazon Echo Show®; Amazon Echo Dot®; Smart Television (e.g., Samsung® Smart TVs); Google Home®; Apple Siri-enabled devices; "OK Google" enabled devices; Voice Controlled Thermostats (e.g., Nest®; Honeywell® Wi-Fi Smart Thermostat with Voice Control), smart vehicles, smart transportation devices, wearable devices (e.g., Fitbit®), and/or smart accessories, to name a few.

In embodiments, the subject may verbalize one or more words and/or phrases as part of a request for attention from the healthcare provider (hereinafter "Request"). The Request, in embodiments, may be detected by the microphone 110 of the portable electronic device 102 and/or the microphone operatively connected to the portable electronic device 102. The subject, for example, may say a Request—e.g. "I need water." The Request, as used herein, may refer to any question, request, comment, word, words, phrases, and/or instructions that may be spoken to the microphone 110 of the portable electronic device 102 and/or the microphone operatively connected to the portable electronic device 102.

The Request, in some embodiments, may be prefaced by a wakeword, which may also be referred to as a trigger expression, wake expression, or activation word. In response to detecting an utterance of the wakeword, portable electronic device 102 may be configured to detect and interpret any words that subsequently follow the detected wakeword as actionable inputs or commands. In some embodiments, the portable electronic device 102 may be activated by a phrase or grouping of words, which the portable electronic device 102 may also be configured to detect. The portable electronic device 102, therefore, may also be able to detect and interpret any words subsequently following that phrase or grouping of words. For example, the subject may state "Health Request" before stating a response. In embodiments, no wakeword may be required for the portable electronic device 102 and/or the microphone 110 to detect and analyze audio data associated with the Request. For example, the portable electronic device 102 may be configured to listen for an answer in the form of audio data once receiving a physical input via the input device 108.

As used herein, the term "wakeword" may correspond to a "keyword" or "key phrase," an "activation word" or "activation words," or a "trigger," "trigger word," or "trigger expression." One exemplary wakeword may be a phrase, such as the phrase, "Health Request," however it should be appreciated that any word, or series of words may alternatively be used as the wakeword. Furthermore, the wakeword may be set or programmed by a healthcare provider and/or the subject, and in some embodiments more than one wakeword (e.g., two or more different wakewords) may be available for use. In yet another embodiment, the trigger that is used to activate the portable electronic device 102 may be any series of temporally related sounds.

In embodiments, the microphone 110 and/or the microphone (hereinafter the "Microphone(s)") may detect the spoken Request using one or more microphones resident thereon. After detecting the Request, the microphone may send audio data representing Request to the processor(s) 118 of the portable electronic device 102. Alternatively, the microphone 110 may detect the Response and transmit the response to the portable electronic device 102 and processor 118. The microphone 110 may also send one or more additional pieces of associated data to the portable electronic device 102. Various types of associated data that may be included with the audio data include, but are not limited to, a location of the subject, identity information, medical information, a time of the Request, a date that the Request was detected, an IP address associated with the computer device 102, a type of device, or any other type of associated data, or any combination thereof, to name a few.

The audio data and/or associated data, if detected by a microphone operatively connected to the portable electronic device 102 may be transmitted over a network, such as the Internet, to the computing device 102 using any number of communications protocols. For example, Transfer Control Protocol and Internet Protocol ("TCP/IP") (e.g., any of the protocols used in each of the TCP/IP layers), Hypertext Transfer Protocol ("HTTP"), and wireless application protocol ("WAP"), are some of the various types of protocols that may be used to facilitate communications between the microphone and the portable electronic device 102.

The portable electronic device 102 may be operatively connected to one or more servers, each in communication with one another, additional microphones, and/or output electronic devices (e.g. display 124, audio output 112, and/or LED(s) 106), to name a few. Portable electronic device 102, one or more servers, additional microphones, and/or output electronic device may communicate with each other using any of the aforementioned communication protocols. Each server operatively connected to the portable electronic device 102 may be associated with one or more databases or processors that are capable of storing, retrieving, processing, analyzing, and/or generating data to be provided to the portable electronic device 102. For example, each of the one or more servers may correspond to a different type of medical device, enabling natural language understanding to account for different types of scientific words. The one or more servers, may, in some embodiments, correspond to a collection of servers located within a remote facility, and care givers and/or the subject may store data on the one or more servers and/or communicate with the one or more servers using one or more of the aforementioned communications protocols.

Referring back to portable electronic device 102, once portable electronic device 102 receives the audio data, portable electronic device 102 may analyze the audio data by, for example, performing speech-to-text (STT) processing on the audio data to determine which words were included spoken Request. Portable electronic device 102 may then apply natural language understanding (NLU) processing in order to determine the meaning of spoken Request. Portable electronic device 102 may further determine whether the Request indicates an emergency and cause the LED(s) 106 to illuminate and/or an alarm to sound. In embodiments, the meaning of the Request may also cause the portable electronic device 102 to send a notification and/or a request to the nurse call station.

In embodiments, the portable electronic device 102 may provide an audio and/or visual response to the Response. For example, in some embodiments, the response to spoken Request may include an audio response indicating that the request is being adhered to by one or more healthcare providers. Upon determining that the content should be output, the portable electronic device 102 may generate first responsive audio data by obtaining text data representing the first responsive audio data and using text-to-speech (TTS) processing. The first responsive audio data may represent a first audio message notifying the subject that the Request is $3^{rd}$ in the que and will be addressed soon. Portable electronic device 102 may play the responsive audio data through audio output 112 and/or send the responsive audio data to speakers operatively connected to the portable electronic device 102 such that the responsive audio data will play upon receipt.

As noted above, the portable electronic device 102 may also send the content responsive to spoken Request to display 124. For example, in some embodiments, portable electronic device 102 may determine that the Request is for company and the response may be a short motivational video from one or more of the category servers and send the content, along with instructions to display the content, to display 124. Upon receiving the content and instructions, display 124 may display the content.

Figure 3A:
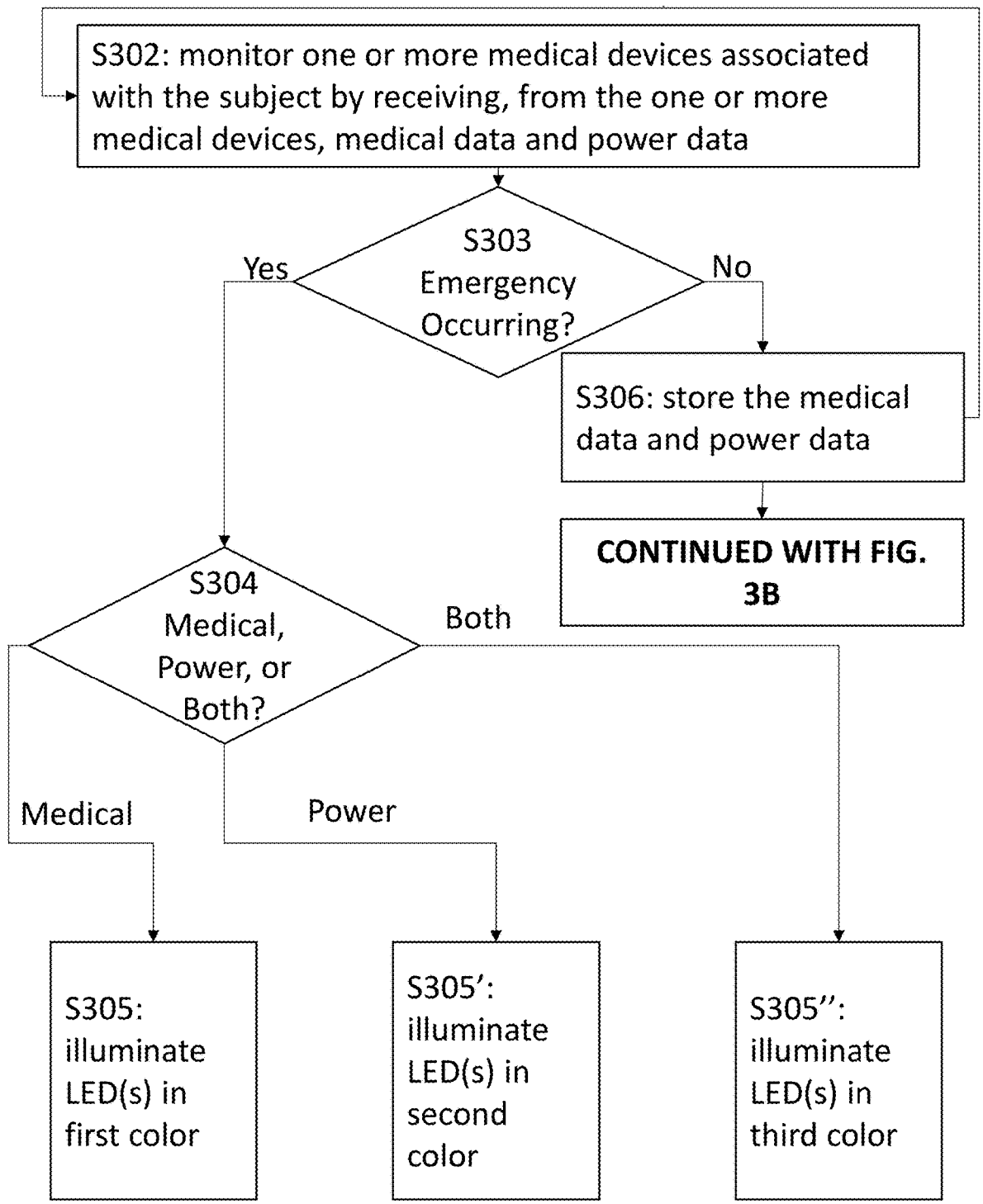
FIGS. 3A-3B are exemplary flow charts of processes for providing healthcare to one or more patients in a remote location in accordance with various embodiments of the present invention.
Figure 3B:
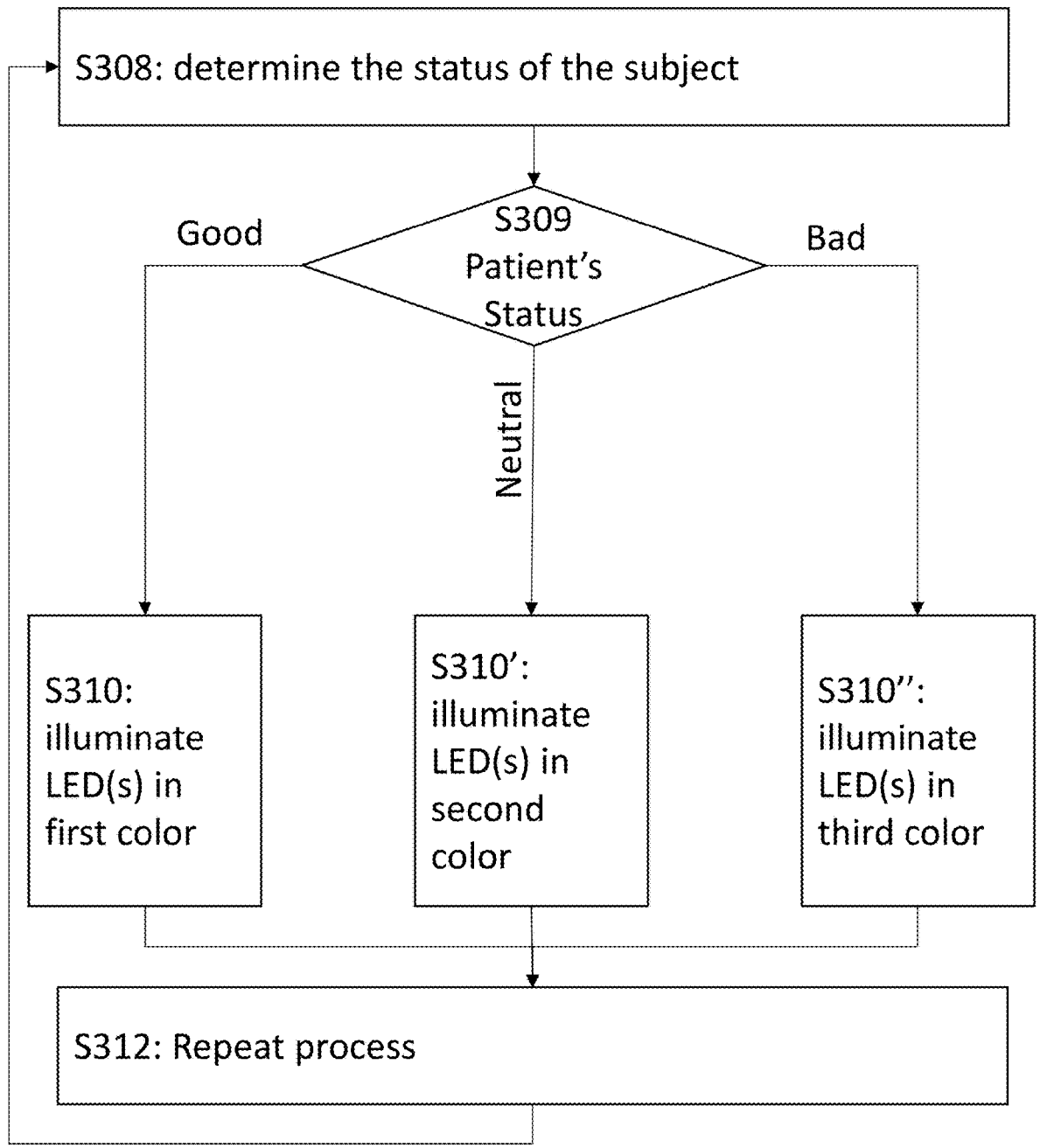

FIGS. 3A-3B are exemplary flow charts of processes for providing healthcare to one or more patients in a remote location in accordance with various embodiments of the present invention.

The process of FIG. 3A, in embodiments, may begin with step S302. At step S302, in embodiments, the portable electronic device 102 monitors one or more medical devices associated with the subject by receiving, from the one or more medical devices, medical data and power data. Medical data, in embodiments, may be data from one or more medical devices being monitored by the portable electronic device 102 and may include one or more of the following: body temperature, oxygen levels, medication administration, heart rate, blood pressure, sugar levels, potassium levels, and/or a combination thereof, to name a few. Power data, in embodiments, may include one or more of the following: remaining power of the one or more medical devices, a low battery indicator, a dead battery indicator, how much life in is left in a battery, and/or a combination thereof, to name a few.

In embodiments, the medical data and power data received by the portable electronic device 102 may be monitored for emergencies. In embodiments the data may indicate a medical emergency is occurring. For example, the medical data could indicate an oxygen level that is not safe for the subject. In embodiments where a medical emergency is occurring, the process may continue with step S304. At step S304, the portable electronic device 102 may illuminate one or more of the LED(s) 106 in a first color (e.g. red). The portable electronic device 102 may send a notification to a nurse call station and/or to a healthcare provider, indicating the health emergency. In embodiments, the LED(s) 106 may also blink. In embodiments, a medical emergency may cause the portable electronic device 102 to call a healthcare provider (e.g. Facetime using display 124, audio via microphone 110 and/or audio output 112, to name a few).

In embodiments the data may indicate a power emergency is occurring. For example, the power data could indicate a ventilator is running low on power. In embodiments where a power emergency is occurring, the process may continue with step S304'. At step S304', the portable electronic device 102 may illuminate one or more of the LED(s) 106 in a second color (e.g. orange). The portable electronic device 102 may send a notification to a nurse call station and/or to a healthcare provider, indicating the power emergency and/or the medical device associated with the emergency. In embodiments, the LED(s) 106 may also blink.

In embodiments the data may indicate a medical and a power emergency are both occurring. For example, the power data could indicate a ventilator is running low on power and the medical emergency may be a drop in oxygen levels of the subject. In embodiments where both a medical emergency and a power emergency are occurring, the process may continue with step S304". At step S304", the portable electronic device 102 may illuminate one or more of the LED(s) 106 in a third color (e.g. yellow). The portable electronic device 102 may send a notification to a nurse call station and/or to a healthcare provider, indicating the health emergency and the power emergency and/or the medical device associated with the emergency. In embodiments, the LED(s) 106 may also blink.

In embodiments, the medical data and power data received by the portable electronic device 102 may not indicate an emergency is occurring. In embodiments, the process may continue with step S306. At step S306, in embodiments, the medical data and power data may be stored in memory 116. In embodiments, as shown in FIG. 3A, the process may repeat, continuously monitoring for an emergency. In embodiments, the process may continue with FIG. 3B.

Referring to FIG. 3B, in embodiments, the process may continue with step S308. At step S308, in embodiments, the portable electronic device may determine the status of the patient. In embodiments, the status, may refer to the health status, medication status (e.g. was medication recently administered), mental health status, and/or a combination thereof, to name a few. The status, in embodiments, may be determined by comparing the medical data received by the portable electronic device 102 to the medical data stored by the portable electronic device 102 in memory 114. If the data, in embodiments, indicates the patient is in a stable (e.g. good) status, the process may continue with step S310. At step S310, in embodiments, the portable electronic device 102 may illuminate one or more of the LED(s) in a first color (e.g. green). The portable electronic device 102 may send a notification to a nurse call station and/or to a healthcare provider, indicating the status of the subject. In embodiments, the LED(s) 106 may also blink. In embodiments, the audio output may also play an audio file.

If the data, in embodiments, indicates the patient is in a neutral (e.g. no change) status, the process may continue with step S310'. At step S310', in embodiments, the portable electronic device 102 may illuminate one or more of the LED(s) in a second color (e.g. yellow). The portable electronic device 102 may send a notification to a nurse call station and/or to a healthcare provider, indicating the status of the subject. In embodiments, the LED(s) 106 may also blink. In embodiments, the audio output may also play an audio file.

If the data, in embodiments, indicates the patient is in a bad (e.g. negative or negative change) status, the process may continue with step S310". At step S310", in embodiments, the portable electronic device 102 may illuminate one or more of the LED(s) in a third color (e.g. red). The portable electronic device 102 may send a notification to a nurse call station and/or to a healthcare provider, indicating the status of the subject. In embodiments, the LED(s) 106 may also blink. In embodiments, the audio output may also play an audio file.

In embodiments, a change in status may cause the portable electronic device 102 to alert the nurse call station about the change in status.

The process may be repeated, as in step S312, until the subject has been completely treated. In embodiments, the steps of the process described in connection with FIGS. 3A and 3B may be rearranged or omitted.

As the above documents, this invention overcomes the technical problems described above.

While this invention has been described in conjunction with the exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. A portable electronic device to provide healthcare to a subject at a remote location, the portable electronic device comprising:
    (a) a housing;
    (b) a power source operable to provide power to the portable electronic device;
    (c) a plurality of light emitting diodes electrically coupled to the power source,
        wherein each of the plurality of light emitting diodes is operable to:
            i. emit one or more colors; and
            ii. blink, and
        wherein each of the plurality of light emitting diodes is positioned such that light emitted from each of the plurality of light emitting diodes is visible outside the housing;
    (d) a communication portal electrically coupled to the power source,
        wherein at least a portion of the communication portal is located inside the housing; and
    (e) an input device electrically coupled to the power source and operatively connected to the plurality of light emitting diodes and the communication portal,
        wherein the input device is located outside the housing and is electrically coupled to the power source via an electrical cord,
    wherein the portable electronic device is operable to be mechanically coupled to one or more patient devices associated with the subject,
    wherein the portable electronic device is operable to provide a notification to one or more healthcare providers associated with the subject, and
    wherein the portable electronic device is configured to perform the following steps:
        A. receive, at the input device, an input from the subject indicating attention from the one or more healthcare providers is requested by the subject; and
        B. illuminate, in response to the input from the subject, one or more of the plurality of light emitting diodes.

2. The portable electronic device of claim 1, further comprising:
    (f) a hook outside the housing and mechanically coupled to the housing,
        wherein the hook is operable to be mechanically coupled to the one or more patient devices.

3. The portable electronic device of claim 2, wherein the one or more patient devices includes an IV for infusion.

4. The portable electronic device of claim 1, wherein the input device comprises:
    i. a patient input device operable to receive a first one or more inputs which indicate attention from the one or more healthcare providers is requested by the subject; and
    ii. a healthcare provider input device operable to receive a second one or more inputs which indicate attention from the one or more healthcare providers has been provided to the subject.

5. The portable electronic device of claim 1, wherein the communication portal comprises:
    i. an infra-red receiver operable to receive communication from a nurse call station associated with the one or more healthcare providers,
        wherein the infra-red receiver is at least partially outside the housing; and
    ii. an infra-red transmitter operable to send communication to the nurse call station.

6. The portable electronic device of claim 1, wherein the communication portal comprises:
    i. an antenna operable to receive radio frequencies from a nurse call station associated with the one or more healthcare providers,
        wherein the antenna is at least partially outside the housing; and
    ii. a radio frequency transmitter operable to send radio frequencies to the nurse call station.

7. The portable electronic device of claim 1, further comprising:
    (f) memory, inside the housing and electrically coupled to the power source, configured to store:
        i. identity information associated with the subject; and
        ii. medical information associated with the subject.

8. The portable electronic device of claim 1, further comprising:

(f) a computing device, at least partially inside the housing and electrically coupled to the power source, configured to:
  i. monitor one or more medical devices associated with the subject by receiving, from the one or more medical devices, one or more of the following:
    1. medical data associated with a medical condition of the subject,
      wherein the medical data includes biometric information of the subject, and
      wherein the medical data is obtained by the one or more medical devices;
    2. power data associated with a power supply of the one or more medical devices,
      wherein the power data indicates one or more of the following:
        A. whether the one or more medical devices is receiving electrical power; and
        B. an amount of electrical power remaining from one or more power supplies corresponding to the one or more medical devices;
  ii. determine whether an emergency is occurring by determining whether the medical data associated with the medical condition of the subject indicates the emergency;
  iii. determine whether the one or more medical devices has sufficient power by comparing the power data to a predetermined amount;
  iv. in the event of the emergency occurring, cause one or more of the plurality of light emitting diodes to illuminate; and
  v. in the event one or more of the one or more medical devices does not have sufficient power, cause one or more of the plurality of light emitting diodes to illuminate.

9. The portable electronic device of claim 8, wherein the portable electronic device is further configured to:
  A. in the event of the emergency occurring, send a first notification to a nurse call station associated with the one or more healthcare providers,
    wherein the first notification indicates the emergency is occurring; and
  B. in the event one or more of the one or more medical devices does not have sufficient power, send a second notification to the nurse call station indicating the one or more of the one or more medical devices not having sufficient power.

10. The portable electronic device of claim 8, wherein the computing device is further configured to:
  vi. store, in memory operatively connected to the portable electronic device, the received medical data and the received power data;
  vii. monitor, based on medical data received and medical data stored, a status of the subject;
  viii. determine, based on medical data received and medical data stored, the status of the subject based on one or more of the following:
    1. comparing the medical data received to typical healthy medical data;
    2. comparing the medical data received to medical information associated with the subject; and
    3. comparing the medical data received to medical data stored to determine a status trend associated with the subject;
  ix. in the event the status of the subject is a negative status, cause one or more of the plurality of light emitting diodes to illuminate in a first color,
    wherein the first color indicates the negative status of the subject;
  x. in the event the status of the subject is a positive status, cause one or more of the plurality of light emitting diodes to illuminate in a second color,
    wherein the second color indicates the positive status of the subject; and
  xi. in the event the status of the subject is a neutral status, cause one or more of the plurality of light emitting diodes to illuminate in a third color,
    wherein the third color indicates the neutral status of the subject.

11. The portable electronic device of claim 10, wherein the portable electronic device is further configured to:
  A. send a first notification to a nurse call station associated with the one or more healthcare providers,
    wherein the first notification indicates the status of the subject.

12. The portable electronic device of claim 11, wherein the portable electronic device is further configured to:
  B. in the event the status of the subject changes, send a second notification to the nurse call station indicating the status of the subject changing.

13. The portable electronic device of claim 10, further comprising
  (g) an audio output electrically coupled to the power source, wherein the audio output is configured to:
    i. in the event of the emergency occurring, play a first alarm;
    ii. in the event one or more of the one or more medical devices does not have sufficient power, play a second alarm; and
    iii. in the event the status of the subject is a negative status, play a third alarm.

14. The portable electronic device of claim 10, further comprising
  (g) an audio output electrically coupled to the power source, wherein the audio output is configured to, in response to the input from the subject, play an alarm.

15. The portable electronic device of claim 8, wherein the one or more medical devices includes a ventilator.

16. The portable electronic device of claim 8, wherein the one or more medical devices includes an intravenous control device.

17. The portable electronic device of claim 8, wherein the one or more medical devices includes a medication administering device.

18. The portable electronic device of claim 1, wherein the power source comprises one or more disposable batteries.

19. The portable electronic device of claim 1, wherein the power source comprises one or more rechargeable batteries.

20. The portable electronic device of claim 19, wherein the one or more rechargeable batteries are charged via capacitive coupling.

21. The portable electronic device of claim 1, further comprising:
  (f) one or more sensor devices electrically coupled to the power source, wherein the one or more sensor devices comprises:
    1. a smoke detector comprising an alarm and configured to detect smoke and fire within a predetermined radius of the subject.

22. The portable electronic device of claim 21, wherein the smoke detector is further configured to:
  i. in the event of detecting smoke, activate the alarm;
  ii. in the event of detecting fire, activate the alarm; and
  iii. in the event of low battery, activate the alarm.

23. The portable electronic device of claim 22, wherein the smoke detector is further configured to notify a nurse call station associated with the one or more healthcare providers in the event of detecting smoke, fire, or low battery.

24. The portable electronic device of claim 1, wherein the one or more patient devices includes a wheelchair.

25. The portable electronic device of claim 1, wherein the one or more patient devices includes a gurney.

26. The portable electronic device of claim 1, wherein the one or more patient devices includes a bed.

27. The portable electronic device of claim 1, wherein the one or more patient devices includes a removable pole.

28. The portable electronic device of claim 27, wherein the removable pole includes an intravenous drug delivery mechanism.

29. The portable electronic device of claim 1, further comprising:
    (f) a distribution module electrically coupled between the input device and the communication portal.

* * * * *